United States Patent
Moskowitz et al.

(10) Patent No.: US 9,924,940 B2
(45) Date of Patent: *Mar. 27, 2018

(54) BI-DIRECTIONAL FIXATING TRANSVERTEBRAL BODY SCREWS, ZERO-PROFILE HORIZONTAL INTERVERTEBRAL MINIPLATES, EXPANSILE INTERVERTEBRAL BODY FUSION DEVICES, AND POSTERIOR MOTION-CALIBRATING INTERARTICULATING JOINT STAPLING DEVICE FOR SPINAL FUSION

(75) Inventors: Mosheh T. Moskowitz, Rockville, MD (US); Nathan C. Moskowitz, Rockville, MD (US)

(73) Assignee: Nathan C. Moskowitz, Rockville, MD (US)

( * ) Notice: Subject to any disclaimer, the term of this patent is extended or adjusted under 35 U.S.C. 154(b) by 878 days.

This patent is subject to a terminal disclaimer.

(21) Appl. No.: 13/093,812

(22) Filed: Apr. 25, 2011

(65) Prior Publication Data

US 2011/0208312 A1 Aug. 25, 2011

Related U.S. Application Data

(60) Continuation of application No. 12/347,990, filed on Dec. 31, 2008, now Pat. No. 7,951,180, which is a
(Continued)

(51) Int. Cl.
*A61B 17/068* (2006.01)
*A61F 2/44* (2006.01)
(Continued)

(52) U.S. Cl.
CPC ...... *A61B 17/0642* (2013.01); *A61B 17/0643* (2013.01); *A61B 17/0682* (2013.01);
(Continued)

(58) Field of Classification Search
CPC .......... A61F 2/4455; A61F 2310/00796; A61F 2002/2835; A61F 2002/3052;
(Continued)

(56) References Cited

U.S. PATENT DOCUMENTS 4,554,914 A * 11/1985 Kapp ................. A61B 17/7068
606/247
4,599,086 A * 7/1986 Doty .......................... 606/86 A
(Continued)

FOREIGN PATENT DOCUMENTS

| FR | 2727003 | 5/1996 |
|---|---|---|
| WO | WO 2004/093749 A1 | 11/2004 |
| WO | WO 2006/091503 A1 | 11/2004 |

OTHER PUBLICATIONS

Vincent C. Traynelis, "Prosthetics and Biologics: The Wave of the Future," Clinical Neurosurgery, vol. 50, Proceedings of the Congress of Neurological Surgeons, Philadelphia, PA 2002, Chapter 9, pp. 207-219.
(Continued)

*Primary Examiner* — Pedro Philogene
(74) *Attorney, Agent, or Firm* — Fish & Richardson P.C.

(57) ABSTRACT

An apparatus and method for joining members together using a self-drilling screw apparatus or stapling apparatus are disclosed. The screw apparatus includes a shell and first and second first screw members having tapered ends and threaded bodies that are disposed within the shell. A drive mechanism rotatably drives the first and second screw members from the shell in opposite directions and causes the screw members to embed themselves in the members to be joined. The screw apparatus can be used to join members such as bones, portions of the spinal column, vertebral bodies, wood, building materials, metals, masonry, or plastics. The stapling apparatus includes first and second lever arms rotatably joined together at a fulcrum, and the lever
(Continued)

arms rotate in opposite directions. First and second cartridges are disposed at the ends of the lever arms. Each cartridge is capable of holding a staple including a bracket, a nail member and an alignment slot. When the ends of the lever arms are rotated towards each other the staples from the cartridges are interlocked. The staples can be also be used to join members such as bones, portions of the spinal column, or vertebral bodies.

32 Claims, 25 Drawing Sheets

Related U.S. Application Data division of application No. 11/208,644, filed on Aug. 23, 2005, now Pat. No. 7,704,279.

(60) Provisional application No. 60/670,231, filed on Apr. 12, 2005.

(51) Int. Cl.
*A61B 17/064* (2006.01)
*A61B 17/70* (2006.01)
*A61F 2/28* (2006.01)
*A61F 2/30* (2006.01)

(52) U.S. Cl.
CPC ........ *A61B 17/7064* (2013.01); *A61F 2/4455* (2013.01); *A61B 2017/0648* (2013.01); *A61F 2002/2835* (2013.01); *A61F 2002/3052* (2013.01); *A61F 2002/3085* (2013.01); *A61F 2002/30525* (2013.01); *A61F 2002/30579* (2013.01); *A61F 2002/30841* (2013.01); *A61F 2002/448* (2013.01); *A61F 2220/0025* (2013.01); *A61F 2310/00796* (2013.01)

(58) Field of Classification Search
CPC .. A61F 2002/30525; A61F 2002/30679; A61F 2002/30841; A61F 2002/3085; A61F 2002/448; A61F 2220/0025; A61B 17/0642; A61B 17/0682; A61B 17/7064; A61B 17/0647; A61B 2017/0648
USPC .................. 606/246, 247, 279, 289, 301; 623/17.11–17.16; 227/175.1, 176.1
See application file for complete search history.

(56) References Cited

U.S. PATENT DOCUMENTS

| | | | |
|---|---|---|---|
| 4,636,217 A * | 1/1987 | Ogilvie | A61F 2/44 606/247 |
| 4,960,420 A | 10/1990 | Goble et al. | |
| 4,994,063 A | 2/1991 | Garner | |
| 4,997,432 A | 3/1991 | Keller | |
| 5,062,850 A * | 11/1991 | MacMillan | A61F 2/44 606/247 |
| 5,123,926 A | 6/1992 | Pisharodi | |
| 5,290,312 A | 3/1994 | Kojimoto et al. | |
| 5,514,180 A | 5/1996 | Heggeness et al. | |
| 5,660,188 A | 8/1997 | Groiso | |
| 5,667,472 A | 9/1997 | Finn et al. | |
| 5,669,912 A | 9/1997 | Spetzler | |
| 5,722,976 A | 3/1998 | Brown | |
| 5,782,832 A | 7/1998 | Larsen et al. | |
| 5,960,522 A | 10/1999 | Boe | |
| 6,106,556 A | 8/2000 | Demopulos et al. | |
| 6,126,689 A | 10/2000 | Brett | |
| 6,224,602 B1 | 5/2001 | Hayes | |
| 6,235,034 B1 | 5/2001 | Bray | |
| 6,322,562 B1 | 11/2001 | Wolter | |
| 6,342,074 B1 | 1/2002 | Simpson | |
| 6,368,350 B1 | 4/2002 | Erickson et al. | |
| 6,375,682 B1 | 4/2002 | Fleischmann et al. | |
| 6,419,704 B1 | 7/2002 | Ferree | |
| 6,454,807 B1 | 9/2002 | Jackson | |
| 6,458,159 B1 | 10/2002 | Thalgott | |
| 6,527,804 B1 | 3/2003 | Gauchet et al. | |
| 6,533,818 B1 | 3/2003 | Weber et al. | |
| 6,572,653 B1 | 6/2003 | Simonson | |
| 6,579,318 B2 | 6/2003 | Varga et al. | |
| 6,582,468 B1 | 6/2003 | Gauchet | |
| 6,629,998 B1 | 10/2003 | Lin | |
| 6,641,614 B1 | 11/2003 | Wagner et al. | |
| 6,716,247 B2 | 4/2004 | Michelson | |
| 6,719,794 B2 | 4/2004 | Gerber et al. | |
| 6,723,126 B1 * | 4/2004 | Berry | A61F 2/4611 606/247 |
| 6,733,532 B1 | 5/2004 | Gauchet et al. | |
| 6,764,491 B2 | 7/2004 | Frey et al. | |
| 6,770,094 B2 | 8/2004 | Fehling et al. | |
| 6,890,355 B2 | 5/2005 | Michelson | |
| 6,904,308 B2 | 6/2005 | Frisch et al. | |
| 6,953,477 B2 * | 10/2005 | Berry | 623/17.11 |
| 6,955,671 B2 | 10/2005 | Uchikubo | |
| 7,028,878 B2 | 4/2006 | Bauer | |
| 7,030,904 B2 | 4/2006 | Adair et al. | |
| 7,037,258 B2 | 5/2006 | Chatenever et al. | |
| 7,097,615 B2 | 8/2006 | Banik et al. | |
| 7,211,112 B2 | 5/2007 | Baynham et al. | |
| 7,232,464 B2 | 6/2007 | Mathieu et al. | |
| 7,238,203 B2 | 7/2007 | Bagga et al. | |
| 7,442,209 B2 | 10/2008 | Michelson | |
| 7,704,279 B2 * | 4/2010 | Moskowitz | A61B 17/0642 606/289 |
| 7,776,047 B2 | 8/2010 | Fanger et al. | |
| 8,268,000 B2 | 9/2012 | Waugh et al. | |
| 2002/0068977 A1 | 6/2002 | Jackson | |
| 2002/0143338 A1 | 10/2002 | Orbay et al. | |
| 2004/0088054 A1 | 5/2004 | Berry | |
| 2004/0177531 A1 | 9/2004 | DiBenedetto et al. | |
| 2004/0186569 A1 | 9/2004 | Berry | |
| 2004/0254644 A1 | 12/2004 | Taylor | |
| 2005/0027362 A1 | 2/2005 | Williams et al. | |
| 2005/0049590 A1 | 3/2005 | Alleyne et al. | |
| 2005/0177235 A1 | 8/2005 | Baynham et al. | |
| 2005/0216084 A1 | 9/2005 | Fleischmann | |
| 2005/0256576 A1 | 11/2005 | Moskowitz et al. | |
| 2005/0261769 A1 | 11/2005 | Moskowitz et al. | |
| 2005/0273170 A1 | 12/2005 | Navarro et al. | |
| 2005/0278026 A1 | 12/2005 | Gordon et al. | |
| 2006/0241621 A1 | 10/2006 | Moskowitz et al. | |
| 2007/0049943 A1 | 3/2007 | Moskowitz et al. | |
| 2007/0167678 A1 | 7/2007 | Moskowitz et al. | |
| 2007/0198089 A1 | 8/2007 | Moskowitz et al. | |
| 2007/0213820 A1 | 9/2007 | Magerl et al. | |
| 2007/0250172 A1 | 10/2007 | Moskowitz et al. | |
| 2008/0033440 A1 | 2/2008 | Moskowitz et al. | |
| 2008/0177307 A1 | 7/2008 | Moskowitz et al. | |
| 2008/0281424 A1 | 11/2008 | Parry et al. | |
| 2009/0105831 A1 | 4/2009 | Jones et al. | |
| 2009/0112271 A1 | 4/2009 | Moskowitz et al. | |
| 2009/0224023 A1 | 9/2009 | Moskowitz et al. | |
| 2009/0234455 A1 | 9/2009 | Moskowitz et al. | |
| 2010/0145460 A1 | 6/2010 | McDonough et al. | |
| 2010/0324606 A1 | 12/2010 | Moskowitz et al. | |
| 2011/0125269 A1 | 5/2011 | Moskowitz et al. | |
| 2011/0137349 A1 | 6/2011 | Moskowitz et al. | |
| 2011/0178600 A1 | 7/2011 | Moskowitz et al. | |
| 2011/0208312 A1 | 8/2011 | Moskowitz et al. | |
| 2011/0288646 A1 | 11/2011 | Moskowitz et al. | |
| 2011/0295327 A1 | 12/2011 | Moskowitz et al. | |
| 2011/0295371 A1 | 12/2011 | Moskowitz et al. | |
| 2011/0307011 A1 | 12/2011 | Moskowitz et al. | |
| 2011/0319935 A1 | 12/2011 | Moskowitz et al. | |
| 2012/0010714 A1 | 1/2012 | Moskowitz et al. | |
| 2012/0330419 A1 | 12/2012 | Moskowitz et al. | |
| 2013/0018468 A1 | 1/2013 | Moskowitz et al. | |
| 2013/0018469 A1 | 1/2013 | Moskowitz et al. | |
| 2013/0018470 A1 | 1/2013 | Moskowitz et al. | |

(56) References Cited

U.S. PATENT DOCUMENTS

| | | |
|---|---|---|
| 2013/0023992 A1 | 1/2013 | Moskowitz et al. |
| 2013/0053962 A1 | 2/2013 | Moskowitz et al. |
| 2013/0173002 A1 | 7/2013 | Moskowitz et al. |
| 2013/0282017 A1 | 10/2013 | Moskowitz et al. |
| 2014/0249629 A1 | 9/2014 | Moskowitz et al. |
| 2015/0025637 A1 | 1/2015 | Moskowitz et al. |
| 2015/0105824 A1 | 4/2015 | Moskowitz et al. |
| 2015/0148847 A1 | 5/2015 | Moskowitz et al. |
| 2016/0374830 A1 | 12/2016 | Moskowitz et al. |
| 2017/0252178 A1 | 9/2017 | Moskowitz et al. |

OTHER PUBLICATIONS

E.K. Wai et al., "Disk Replacement Arthroplasties: Can the Success of Hip and Knee Replacements be Repeated in the Spine?," Seminars in Spine Surgery, vol. 15, No. 4 Dec. 2003, pp. 473-482.

Richard D. Guyer et al., "Intervertebral Disc Prostheses," Spine Journal, vol. 28, No. 15S, Supp. To Aug. 1, 2003, pp. S15-S23.

International Search Report (ISR) and Written Opinion of the International Searching Authority, dated Dec. 3, 2007, International Application No. PCT/US 07/05005.

International Search Report (ISR) and Written Opinion of the International Searching Authority, dated May 21, 2008, International Application No. PCT/US2007/021015.

International Search Report (ISR) and Written Opinion of the International Searching Authority, dated Jul. 9, 2008, International Application No. PCT/US2007021013.

* cited by examiner

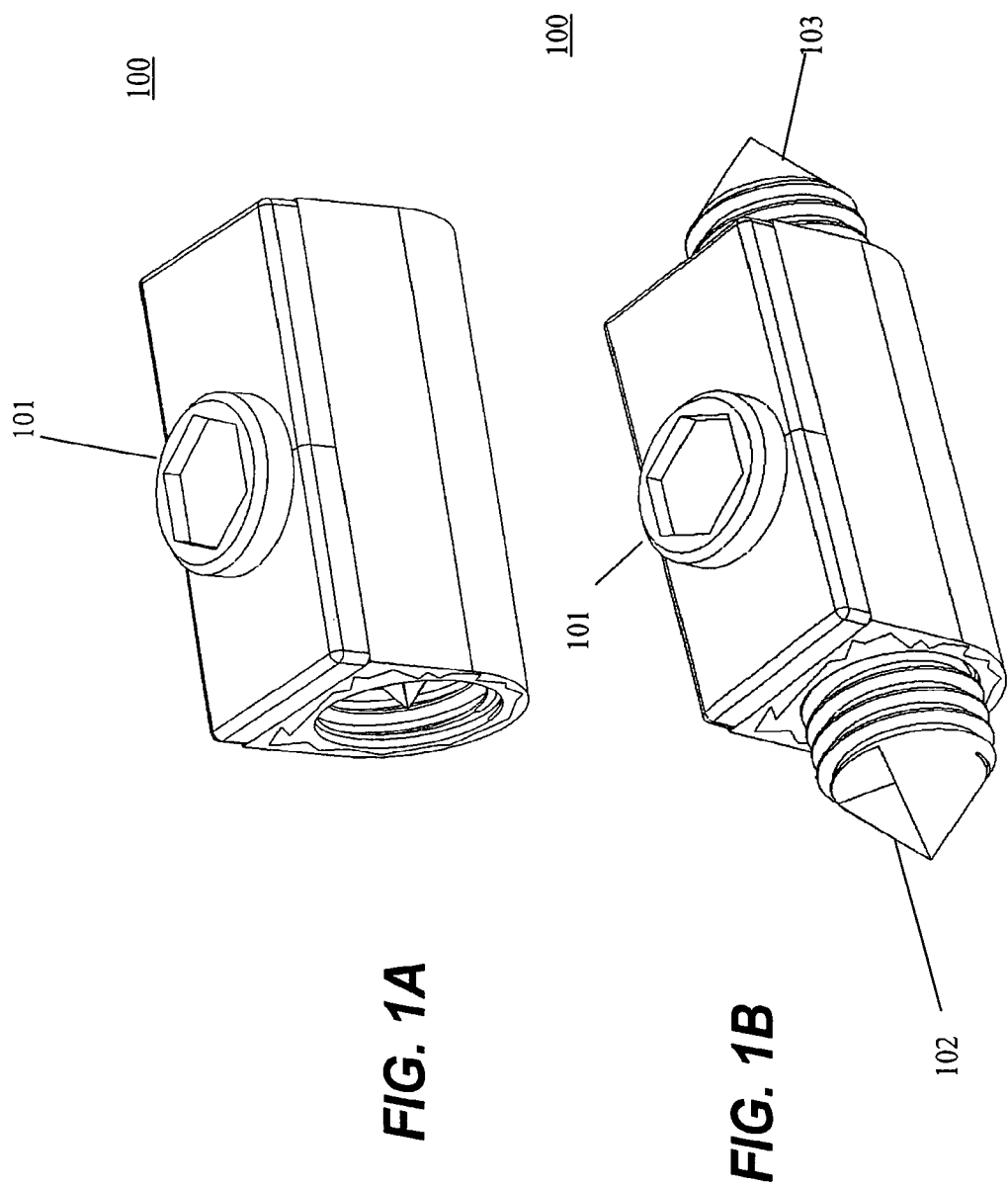

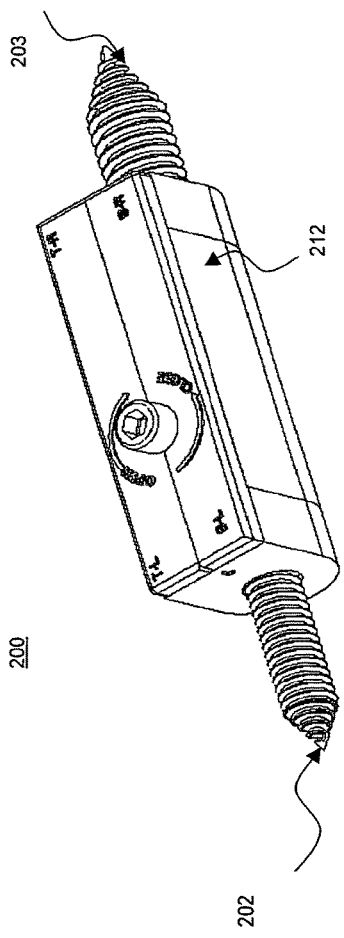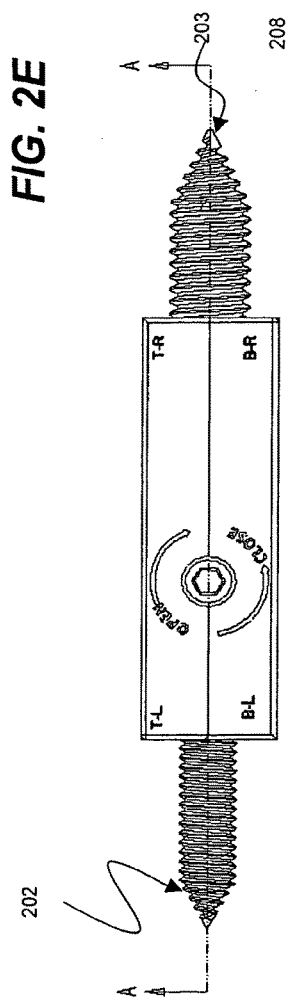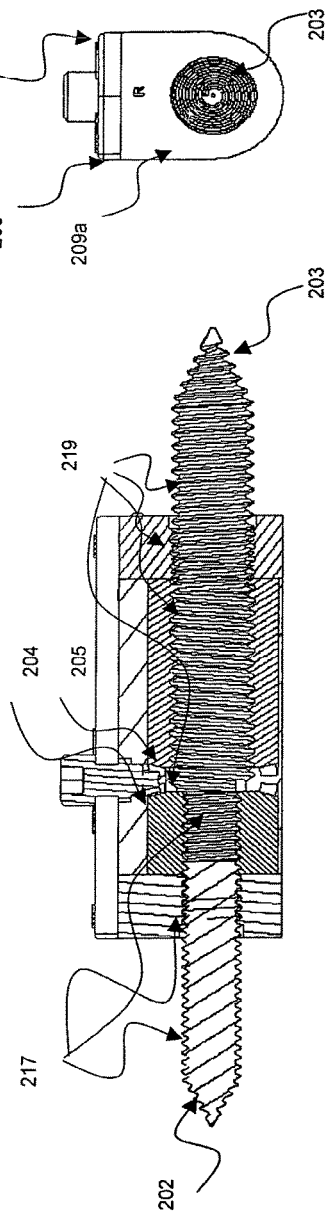
FIG. 2D
FIG. 2E
FIG. 2F
FIG. 2G

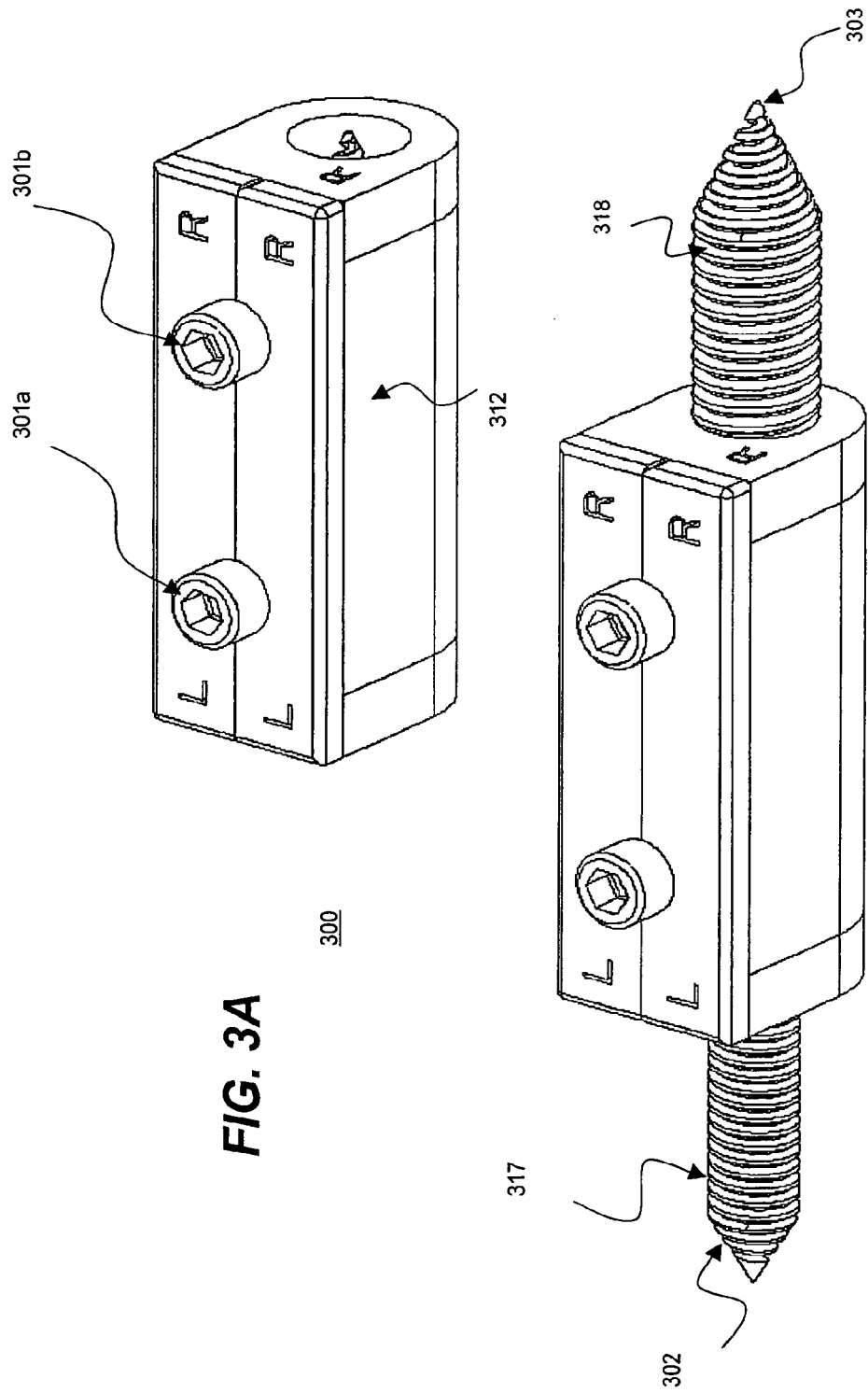

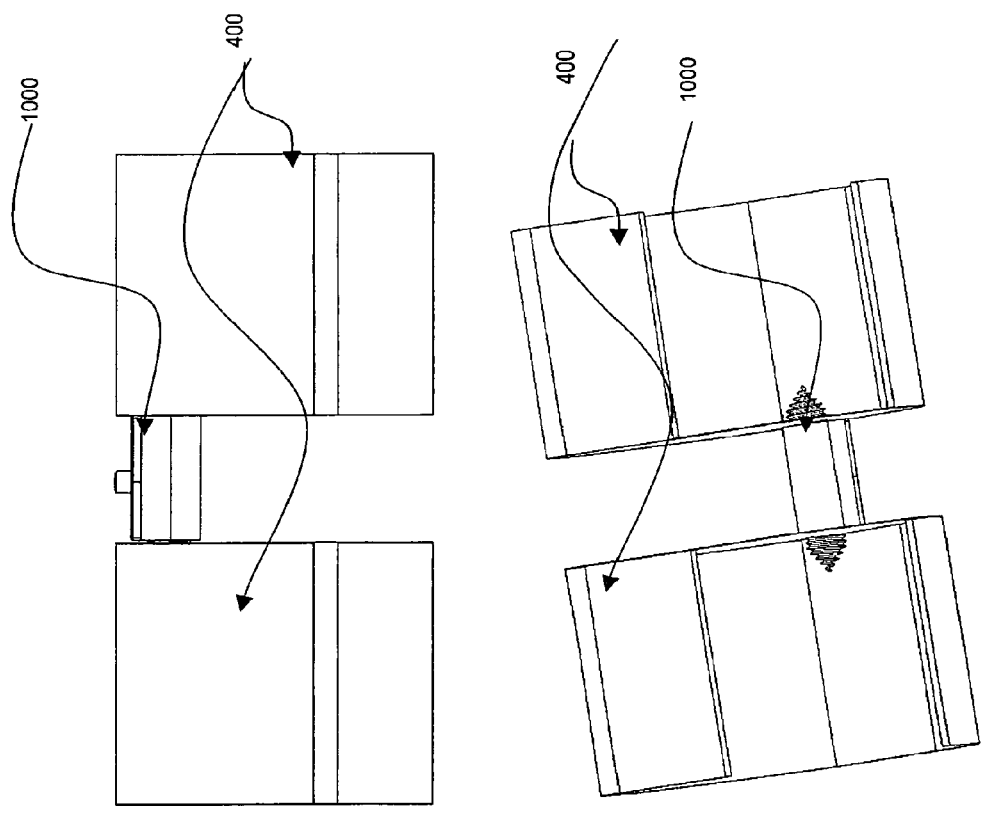

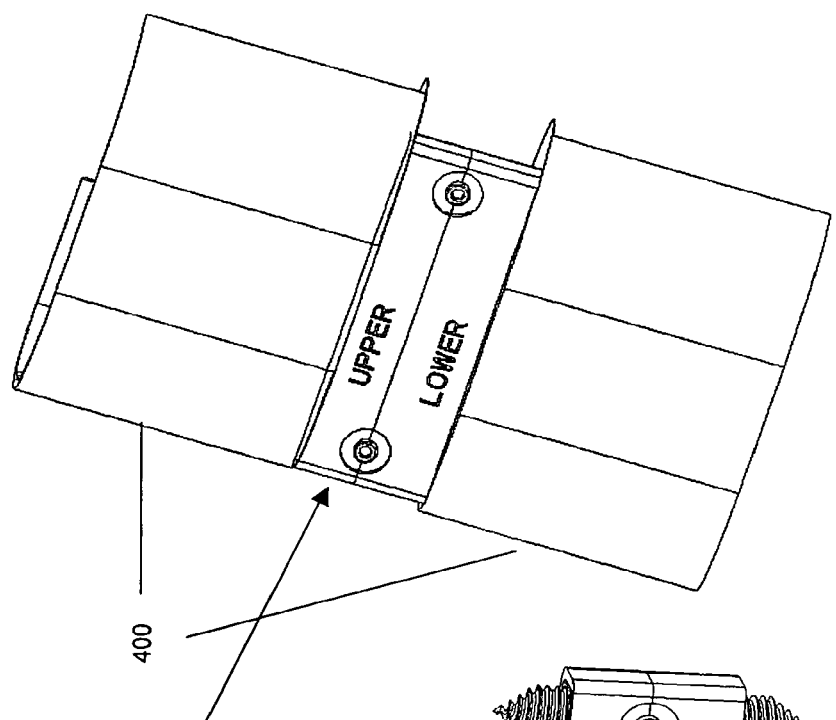
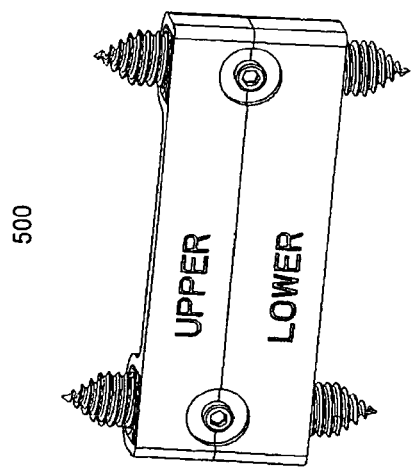
FIG. 5D
FIG. 5C

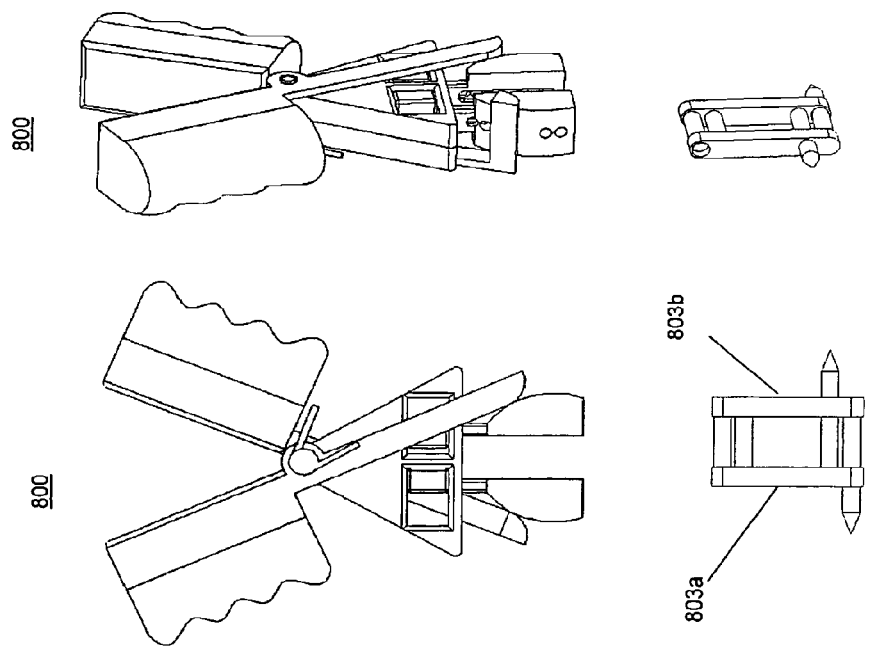

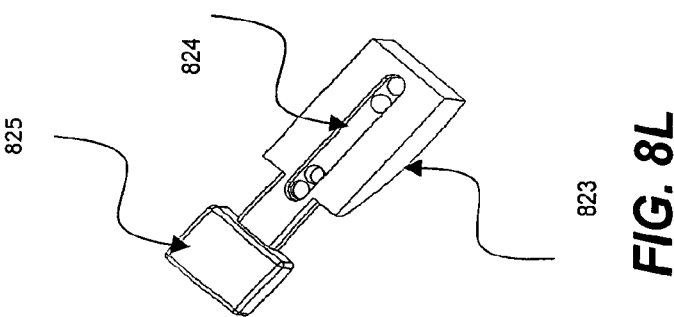
FIG. 8L  FIG. 8K
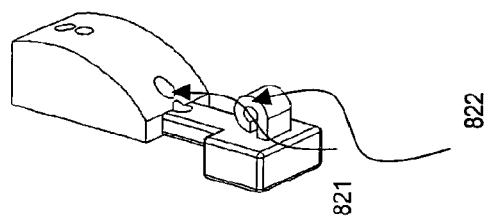
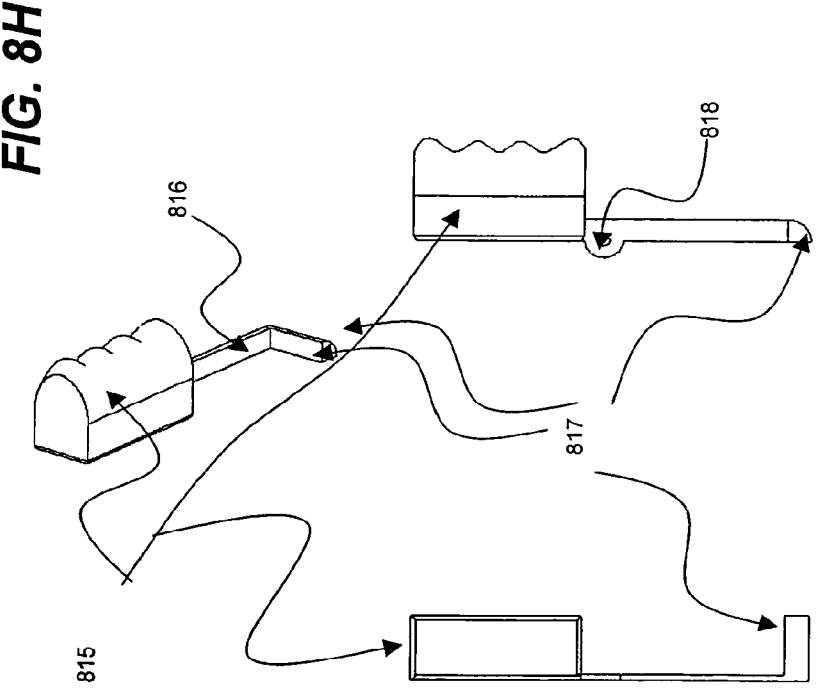
FIG. 8H  FIG. 8I  FIG. 8J

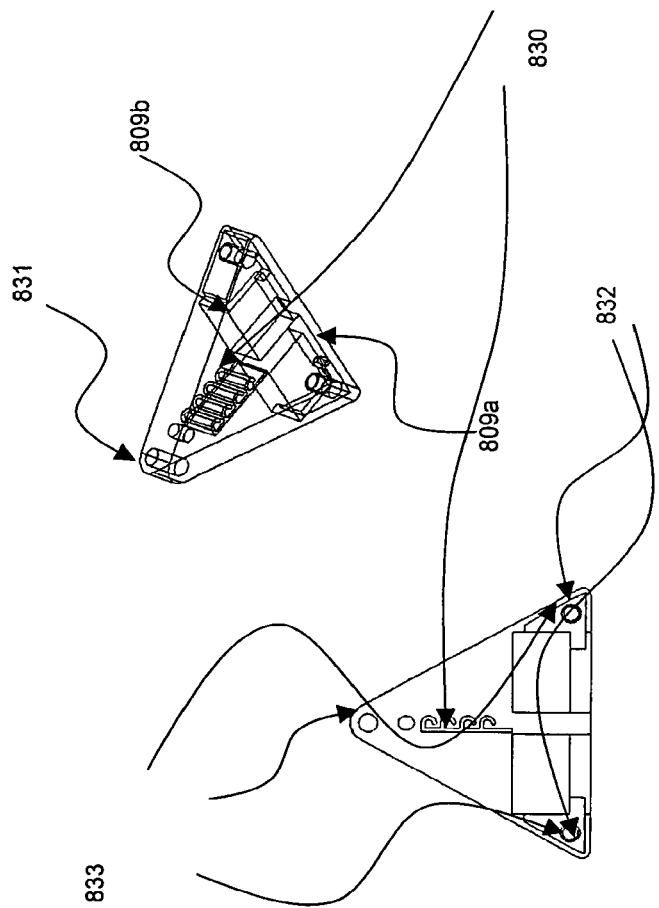

BI-DIRECTIONAL FIXATING TRANSVERTEBRAL BODY SCREWS, ZERO-PROFILE HORIZONTAL INTERVERTEBRAL MINIPLATES, EXPANSILE INTERVERTEBRAL BODY FUSION DEVICES, AND POSTERIOR MOTION-CALIBRATING INTERARTICULATING JOINT STAPLING DEVICE FOR SPINAL FUSION

The present Application is a Continuation Application claiming priority under 35 U.S.C. § 120 of U.S. patent application Ser. No. 12/347,990, filed on Dec. 31, 2008 now U.S. Pat. No. 7,951,180, which is a Divisional Application of U.S. patent application Ser. No. 11/208,644 filed on Aug. 23, 2005 now U.S. Pat. No. 7,704,279, which claims the benefit of priority under 35 U.S.C. § 119(e) of U.S. Provisional Application No. 60/670,231, filed on Apr. 12, 2005; and the entire contents of all the above identified patent applications are hereby incorporated by reference.

FIELD OF INVENTION

The present invention relates to bi-directional fixating transvertebral (BDFT) screws which can be used to supplement other intervertebral spacers and/or bone fusion materials. BDFT screws can be incorporated into anterior and/or posterior cervical and lumbosacral novel zero-profile horizontal and triangular intervertebral mini-plates. In addition BDFT screws can be incorporated into two dimensional, expansile intervertebral body fusion devices (IBFDs) transforming them into stand-alone posteriorly and/or anteriorly placed cervical, thoracic and lumbar spinal fusion devices. In the lumbosacral and thoracic spine BDFT screws may obviate the need for supplemental pedicle screw fixation. In the cervical spine it obviates the need for supplemental vertically oriented anterior plating. The present invention also relates to a stand-alone or supplemental, calibrating interarticular joint stapling device which can incrementally fine-tune posterior interarticular joint motion.

DESCRIPTION OF THE RELEVANT ART

Segmental spinal fusions which stabilize two or more adjacent segments of the spine are performed for painful degenerative disc disease, recurrent disc herniations, spinal stenosis, spondylolysis and spondylolisthesis. Over the past several decades a wide variety of fusion techniques and instrumentation have evolved. One of the earliest posterior fusion techniques entails non-instrumented in-situ on-lay posteriolateral fusion utilizing autologous iliac crest bone. Because of the high rate of imperfect fusions i.e. pseudoarthroses, transpedicular pedicle screw fixation which utilizes a variety of rods and interconnectors were developed to achieve less interbody motion and hence higher fusion rates. Pedicle screw fixation was initially combined with on-lay posteriolateral fusion. Because of the poor blood supply of the transverse processes, issues still remained with pseudoarthroses. In an attempt to address this problem, pedicle screw fixation has been supplemented with a variety of interbody fusion devices. This is based on the concept that axial loading enhances fusion and that the vertebral endplates have a better blood supply. Interbody lumbar fusion devices can be placed anteriorly via an anterior lumbar interbody fusion technique (ALIF) or posteriorly via a posterior lumbar interbody fusion technique (PLIF). Material options for interbody fusion devices have included autologous iliac crest/laminar bone, cylindrical threaded titanium interbody cages, cylindrical threaded cortical bone dowels, vertebral interbody rings or boxes, carbon fiber cages, or femoral ring allograft. To lessen the complication of prolonged nerve root retraction the technique of circumferential transforaminal lumbar interbody fusion technique (TLIF) has been introduced. This employs the transforaminal placement of an interbody spacer such as one kidney bean shaped allograft, two circular allografts, one or two titanium circular cages, a single titanium or Peek (polyether-ketone) boomerang spacer. The threaded spacers are usually supplemented with autologous bone and/or bone morphogenic protein (BMP), demineralized bone matrix (DBM) in the form of paste or cement, rh-BMP with collagen sponges, or similar osteoinductive biological agents which are known to enhance fusion.

Currently all lumbosacral fusion techniques, ALIF, PLIF and TLIF, are typically supplemented by pedicle screw placement. In addition posterior transfacet screws also have been used to supplement ALIF procedures. Complications of pedicle screw placement include duration of procedure, significant tissue dissection and muscle retraction, misplaced screws with neural and/or vascular injury, excessive blood loss, need for transfusions, prolonged recovery, incomplete return to work, excess rigidity leading to adjacent segmental disease requiring further fusions and re-operations. Further advances of pedicle screw fixation including minimally invasive and image-guided technology, and the development of flexible rods have imperfectly addressed some but not all of these issues. Transfacet screws entail the use of long screws which provide a static facet alignment without motion calibration.

Complications of all current interbody fusion devices is their lack of coverage of the majority of the cross sectional area of the vertebral endplates and their potential for extrusion. The recently described flexible fusion system which consists of flexible rods attached to transpedicular screws (Dionysis, Zimmer) suffers from a high pull-out rate, higher rate of re-operation than standard fusions, and does not rank high with patient satisfaction. See for example, *Clinical experience with the Dynesys semirigid fixation system for the lumbar spine: Surgical and patient-oriented outcome in 50 cases after an average of 2 years*; D, Grob, A. Benini and A. F. Mannion. Spine Volume 30, number 3, Feb. 1, 2005.

Single or multiple level anterior cervical spinal fusions typically employ the replacement of the cervical disc or discs with autologous or allograft bone, or an intervertebral spacer filled with autologous or allograft bone, demineralized bone matrix, BMP or rh-BMP etc. Currently these anterior cervical fusions are augmented with anterior vertical titanium plates which cross the intervertebral space or spaces and are secured to the vertebral bodies above and below the disc space or spaces with perpendicularly penetrating vertebral body screws. The purpose of these plates is to serve as a barrier to prevent extrusion of the intervertebral disc replacement. Recently anterior vertical plating has also been employed in anterior lumbar fusion.

Complications of anterior spinal plating include the potential for neurovascular injury with screw misplacement, screw and/or plate pull-out, and screw and/or plate breakage. Other complications include potential esophageal compression/injury in the cervical spine secondary to high plate profile or pull-out, and to potential devastating vascular injury in the lumbar spine with plate movement and/or dislodgement into anterior iliac vasculature. Recent advances in cervical plating have therefore concentrated on the creation of lower profile plates and even resorbable plates. These advances, however, have not eliminated the possibility of plate dislodgement and screw back out/breakage.

To achieve segmental fusion applicants propose the use of novel bi-directional fixating transvertebral (BDFT) screws which can be strategically inserted via anterior or posterior surgical spinal approaches into the anterior and middle columns of the intervertebral disc space. The BDFT mechanism employs turning one or two pinions which then turns one or two central gears which in turn simultaneously controls expansile movement of right and-left-handed bi-directional screws. The vertebral bodies above and below the disc space by virtue of their engagement and penetration by the BDFT screws are thus linked and eventually fused. The casings of the BDFT screws prevent vertebral body subsidence. The inside of the denuded intervertebral space can then be packed with autologous or allograft bone, BMP, DBX or similar osteoinductive material. Alternatively an intervertebral spacer filled with either of these substances can be inserted.

Applicants postulate that BDFT screws provide as strong or stronger segmental fusion as pedicle screws without the complications arising from pedicle screw placement which include screw misplacement with potential nerve and/or vascular injury, violation of some healthy facets, possible pedicle destruction and blood loss. By placing screws across the intervertebral space from vertebral body to vertebral body engaging anterior and middle spinal columns, and not into the vertebral bodies via the transpedicular route, some of the healthy facet joints are preserved. Because this technique accomplishes both anterior and middle column fusion, without rigidly fixing the posterior column, it in essence creates a flexible fusion. This device therefore is a flexible fusion device because the preserved posterior joints retain their function achieving at least a modicum of mobility and hence a less rigid (flexible) fusion.

The very advantage of trans-pedicular screws which facilitate a strong solid fusion by rigidly engaging all three spinal columns (anterior, middle and posterior), is the same mechanical mechanism whereby complete inflexibility of all columns is incurred thereby leading to increasing rostral and caudal segmental stress which leads to an increased rate of re-operation.

Transvertebral fusion also leads to far less muscle retraction, blood loss, and significant reduction in O.R. time. Thus the complication of pedicular screw pull-out and hence high re-operation rate associated with the current embodiment of flexible fusion pedicle screws/rods is obviated. The lumbosacral BDFT screws can be introduced via PLIF, TLIF or ALIF operative techniques. Although one can opt to supplement these screws with transpedicular screws there would be no absolute need for supplemental pedicle screw fixation with these operative techniques.

Bi-directional fixating transvertebral (BDFT) screws can also be combined with novel zero-profile horizontal cervical and lumbar mini-plates. They can also be combined with mini-plates and a cage with slots for bone material insertion. Thus this is in essence a three-in-one device; 1) cage which can be filled with bone, 2) a plate and 3) BDFT screws.

For the performance of anterior cervical, and lumbar anterior or posterior fusions one or two centrally placed BDFT screws anterior to an interverterbal graft or spacer, may be a sufficient barrier by itself to prevent device/graft extrusion. However, to further safeguard against graft/spacer extrusion applicants have devised horizontal linear mini-plates which can be incorporated into two anteriorly placed BDFT screws, as well as a linear triangulating mini-plate which can be incorporated into two anteriorly placed, and one posteriorly placed BDFT screws. The horizontal linear mini-plates or horizontal triangular mini-plate traverse the diameter of the disc space and most of the disc space height. Thus a horizontal mini-plate placed anteriorly immediately beneath the rostral and caudal ventral vertebral body surfaces which is secured by BDFT screws which are also beneath the vertebral body surfaces, would prevent intervertebral device/graft extrusion. This mini-plate is essentially a zero- to sub-zero—profile plate in that it is either flush with the vertebral body surfaces or below them.

Because the BDFT screws engage a small percentage of the rostral and caudal vertebral bodies, this plating system could be performed at multiple levels. This plating system which utilizes BDFT screws does not lead to any esophageal compression or injury in the cervical spine or vascular iliac vein injury in the lumbar spine. For the performance of two or three level intervertebral fusion with horizontal mini-plates there is virtually no possibility of plate breakage which can occur in long vertical anterior plates which are in current usage. Similarly, screw dislodgement, if it occurs would lead to minimal esophageal compression or injury compared to large vertical plate/screw dislodgement. In addition, in the cervical spine BDFT screw placement closer to the midline would avert any possibility of lateral neural or vertebral artery injury.

In copending PCT Patent Application PCT/US2005/016493, filed May 11, 2005, the entire contents of which are incorporated by reference, applicants developed an interbody expansile artificial disc device composed of an inner core artificial disc surrounded by expansile titanium shells with spikes which can expand in two or three dimensions. In yet another embodiment of tranvertebral fixation applicants propose a novel cervical and thoracic/lumbosacral intervertebral fusion device (IBFD) which combines the expansile titanium or PEEK shells or our previous artificial disc design with BDFT screws which can be inserted into the disc space.

Yet another embodiment incorporates a core expansile elastometric porous balloon sheath vulcanized to the expandable external shells which can then be filled with bone fusion material. Balloon porosity would allow fusion to occur from vertebral endplate to endplate. Bony material can be injected into this porous balloon through a port directly or through a silastic catheter (see previous patent).

If one were inclined to further enhance posterior column thoraco-lumbosacral fixation, applicants introduce an optional novel calibrated facet stapling device which staples the inferior articulating facet of the superior segment to the superior articulating facet of the caudal vertebral segment unilaterally or bilaterally, further minimizing motion until interbody fusion occurs. The degree of flexibility can be further modulated by varying the calibration strength and torque of facet stapling. This would be dictated by the need for greater or lesser degrees of motion preservation.

Currently, failed anterior lumbar arthoplasties are salvaged by combined anterior and posterior fusions. BDFT screws and/or IBFDs could be utilized as a one-step salvage operation for failed/extruded anteriorly placed lumbar artificial discs obviating the above salvage procedures which have greater morbidity. Likewise, for anterior cervical fusion, applying cervical BDFT screws alone or in combination with cervical mini-plates addresses the deficiencies and complications of current cervical plating technology as mentioned above.

BRIEF DESCRIPTION OF THE DRAWINGS

FIGS. 1A-D illustrate three-dimensional and cross-sectional views of the BDFT screw and its mechanism of operation (Embodiment I).

FIGS. 2A-G illustrate three-dimensional and cross-sectional views of the BDFT screw and its mechanism of operation (Embodiment II).

FIGS. 3A-E illustrate three dimensional, cross-sectional and exploded views of the BDFT screw and its mechanism of operation (Embodiment III).

FIGS. 4A-C illustrate a single or three BDFT screws inserted into adjacent vertebral bodies.

FIGS. 5C and 5D illustrate the integration of BDFT screws in the zero-profile linear mini-plate.

DETAILED DESCRIPTION OF THE INVENTION

1. The Medical Device

Figure 1C:
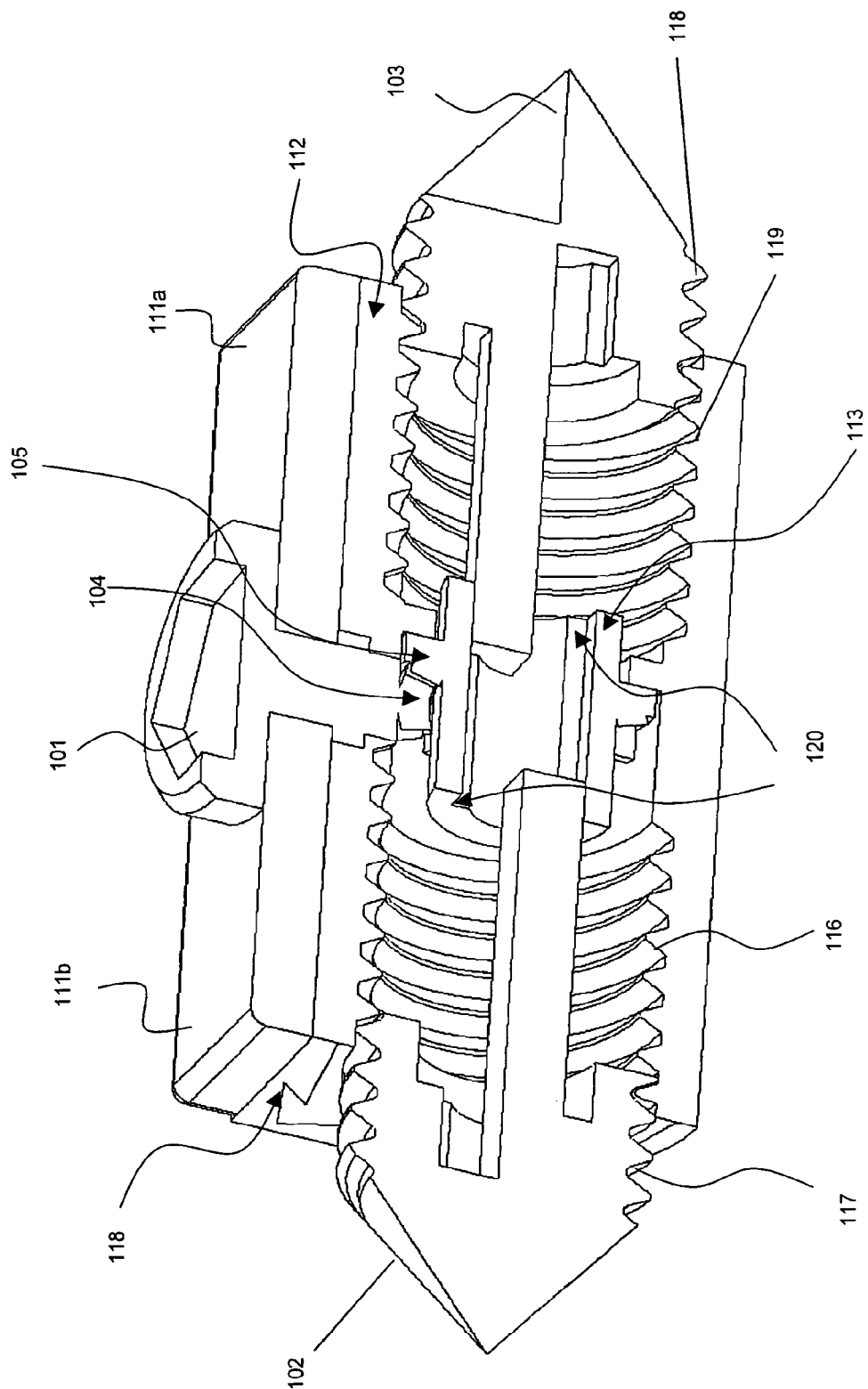
Figure 1D:
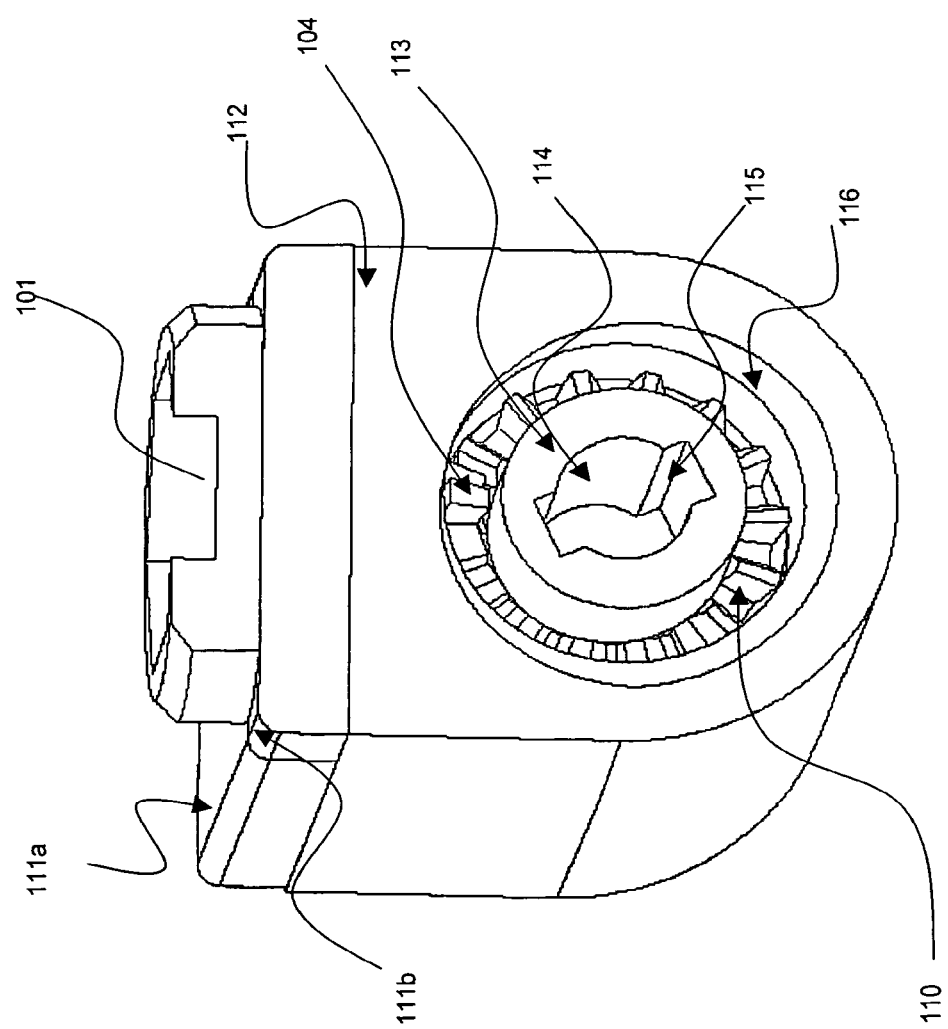
Figure 2A:
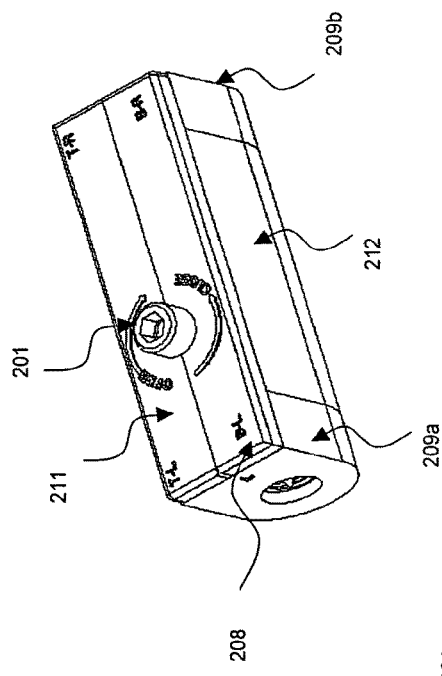
Figure 2B:
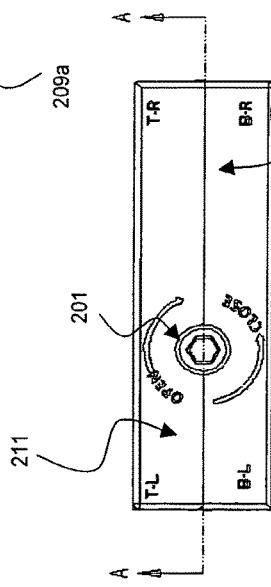
Figure 2C:
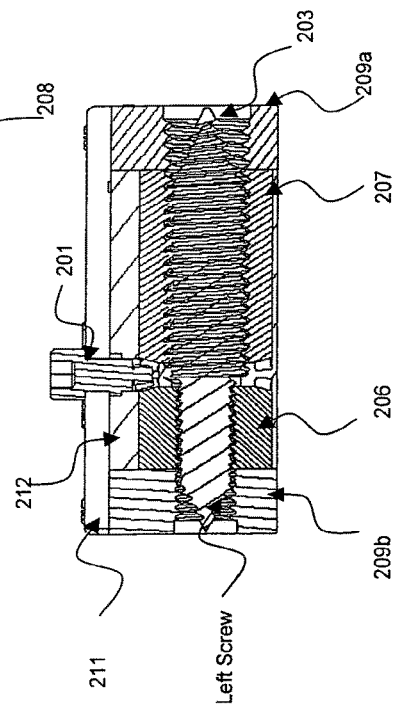
Figures 3C, 3D:
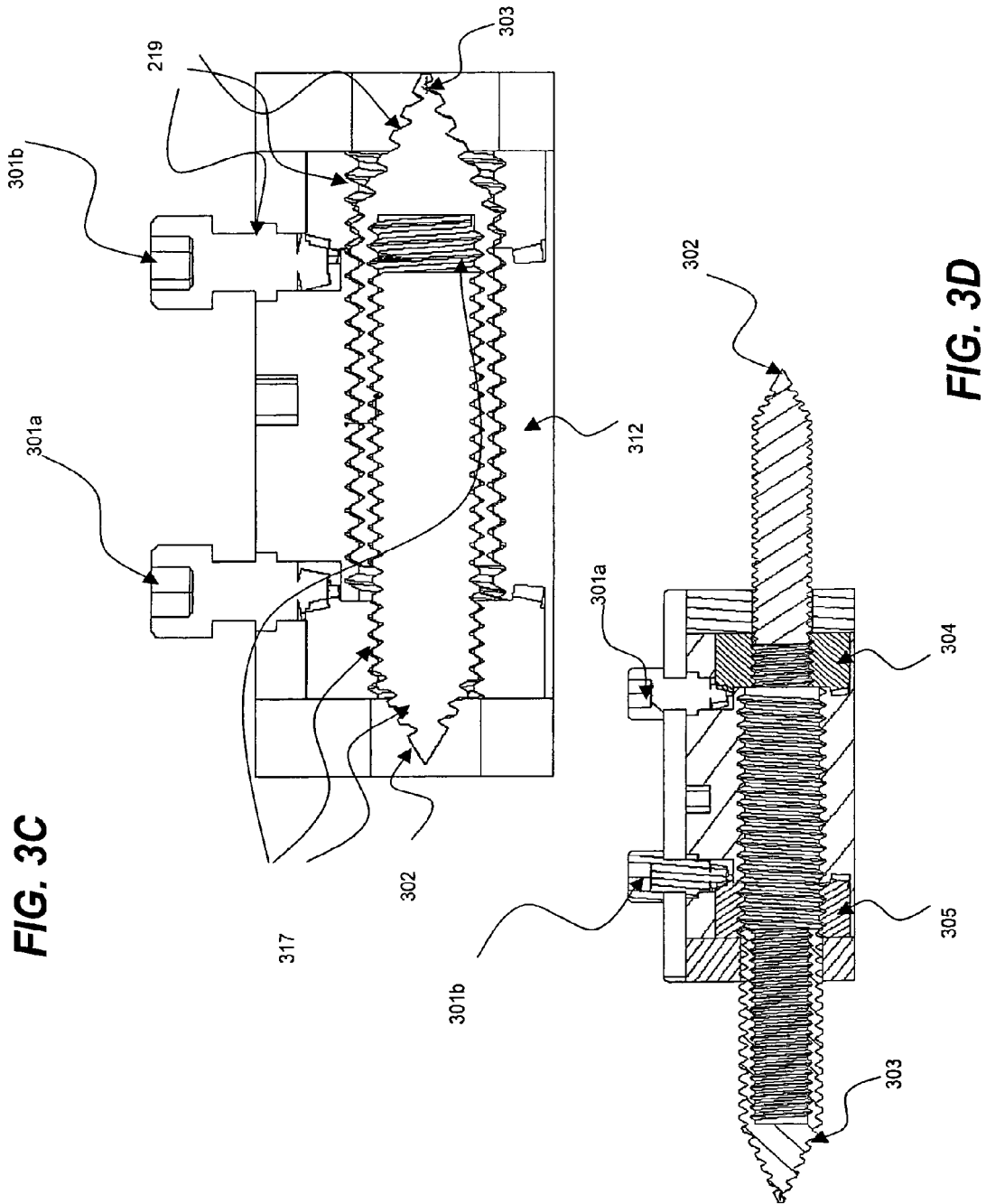
Figure 3E:
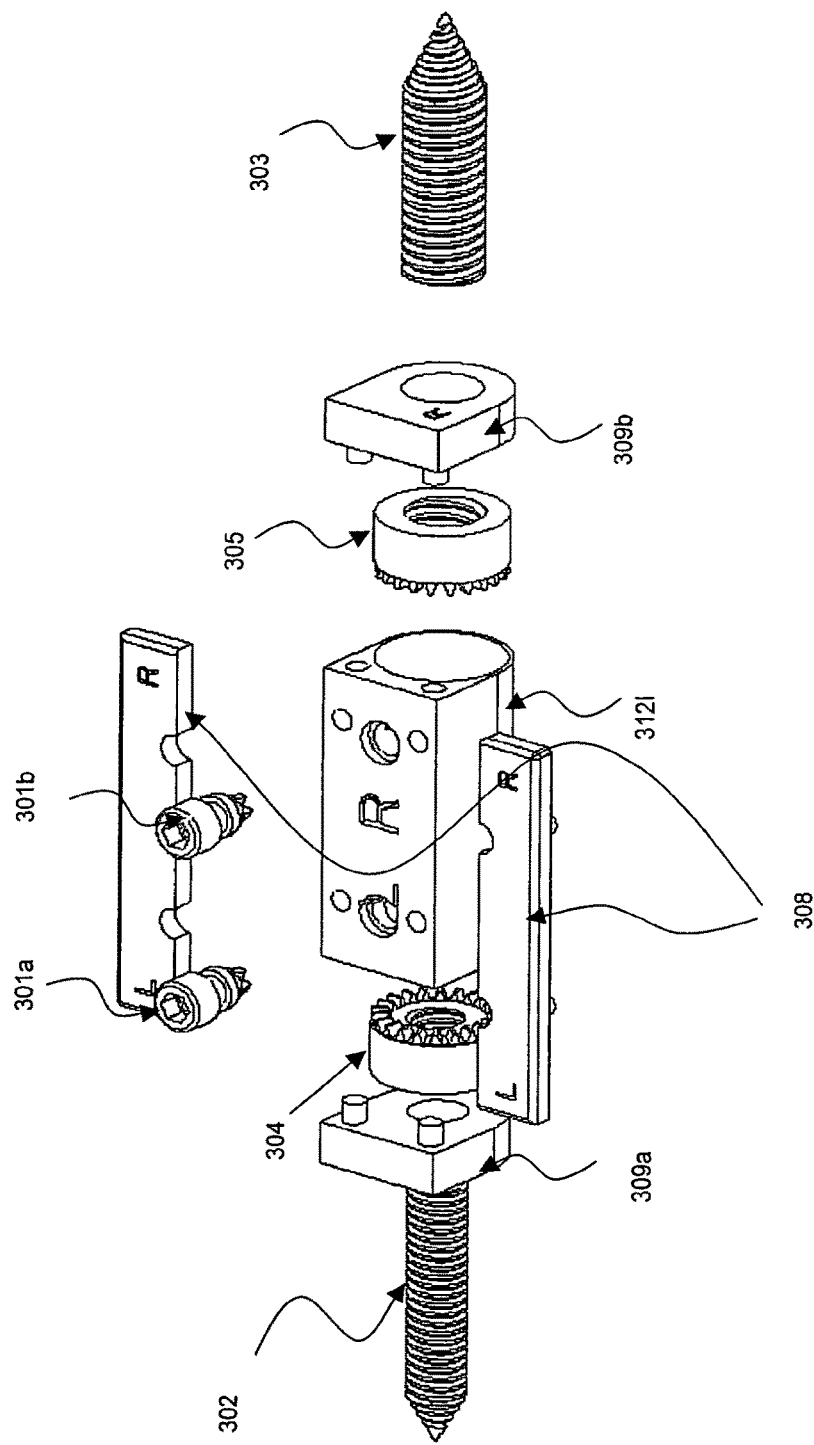

Referring to FIGS. 1A-D the above described problem can be solved in the cervical, thoracic and lumbar spine by insertion into the denuded intervertebral disc space an expansile bi-directional fixating transvertebral (BDFT) screw 100 or screws.

FIGS. 1A and 1B illustrate three-dimensional views of the screw 100 in closed and opened positions, respectively, upon its insertion into the intervertebral disc space. The screw 100 is self-drilling. The mechanism of its action entails the turning of a midline drive screw 100/pinion 104 in a clock-wise direction. This motion is bi-directionally translated via an interposing gear mechanism 105 enabling the simultaneous outward movement of left and right handed screws 102, 103 in equal and opposite directions. When the drive screw 101 and its accompanying drive screw shaft are turned clock-wise, the driving pinion 104 is likewise rotated. This motion is then translated to the driven gear 105 which is interposed between the drive screw 101 and two opposing self-drilling screws 102, 103, one left-handed and the other right-handed. The gear ring 110 has screw coupling slots (Figures IC and 1D). There are also symmetric keyways 120 and an alignment cylinder 113. The left handed screw 102 fits into one half of the slots 114, 115 and the right handed screw 103 into the other half of the slots. This is clearly illustrated in cross sections of the screw and gear in Figures IC and ID, respectively.

FIGS. 1A-C also illustrate the external casing 111 of the device which contains the external screw threads 117, 118, against which the left and right handed internal threads interact 116, 119 with. The casing includes an upper left casing 111b and an upper right casing 111a. Below the upper casing 111b there is a surface serration pattern 118 which is part of a retaining outer shell 112.

FIGS. 2A-G illustrate Embodiment II of the BDFT 200. This design differs in two fundamental ways from Embodiment I. Firstly the driving pinion 201 accomplishes bi-directional movement by engaging left and right gears 204, 205 which simultaneously turn left and right screws 202, 203 (FIGS. 2C-G). Secondly, in it's resting closed position the solid left screw 202 with a narrower diameter is buried within the right wider diameter hollow right screw 203. This mechanism allows for greater length of screw expansion compared to Embodiment I. Maintaining alignment of screws 202, 203 and pinions 201 is accomplished by upper casings 211, outer shells 212, and left and right screw caps 209a, 209b (FIGS. 2A-G).

FIGS. 3A-E illustrate Embodiment III of the BDFT 300. This is similar to Embodiment II. The major difference is the use of two separate driving screws pinions 301a, 301b for the two separate gears 304, 305. There is one pinion 301a for the left screw 302 and another pinion 301b for the right screw 303. The left screw 302 engages the left gear 304 which engages the left screw 302. The right pinion 301a engages the right gear 305 which engages the right screw 303. Because the left and right screws 302, 303 have separate controls and are not linked by one common pinion, separate distinct motions of the screws 302, 303 can be obtained, as opposed to equal and simultaneous screw movements of Embodiments I and II. Like Embodiment II, Embodiment III consists of a smaller diameter solid left screw 302 which fits into a larger diameter hollow right screw 303. This can achieve significant screw extension length as in Embodiment II.

FIGS. 4A and 4B illustrates the placement of a single BTFD 1000 screw anteriorly into the intervertebral space between adjacent lumbar vertebrae 400. FIG. 4A illustrates the closed position. FIG. 4B illustrates the opened position. The illustrations are of a generic BDFT screw 1000 i.e. it applies to Embodiments I-III. Placement of a single BDFT anterior to an intervertbral spacer may be sufficient to prevent interspacer/device extrusion, and enhance spinal stability.

Figure 4C:
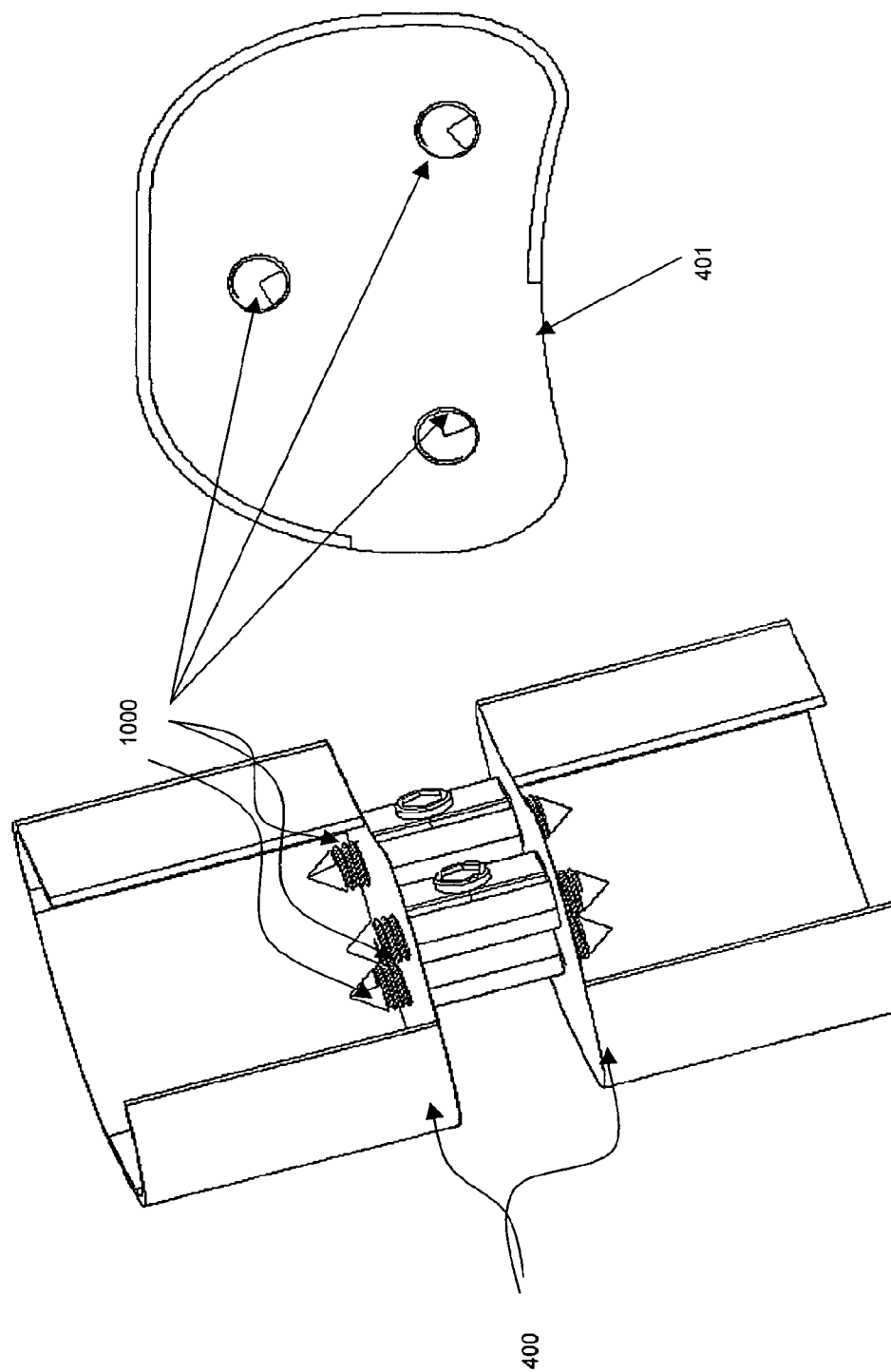

FIG. 4C illustrates the placement of three BTFD screws 1000 in a triangulating manner covering anterior and middle columns. The presence of three screws so situated would prevent subsidence of the screws 1000. Hence they act as a very open IBFD 1000. Bone material in the form of DBX or BMP etc. could be inserted into the intervertebral space in between the three screws 1000. This construct could be used as a supplemental or stand alone-intervertebral fusion device. Also illustrated is a cross-section of a vertebral endplate 401 demonstrating the triangular placement of screws 1000 engaging anterior and middle columns.

Figure 5B:
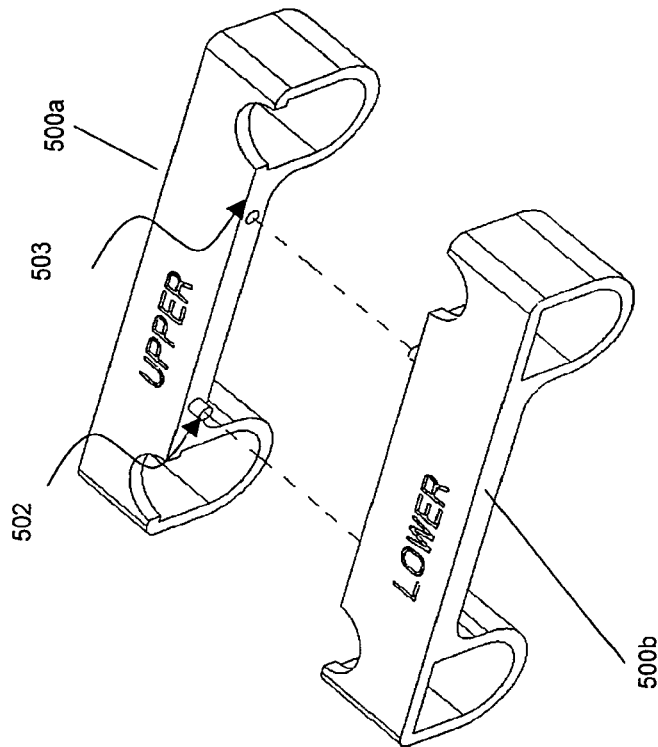
FIGS. 5A and 5B illustrate three-dimensional views of the zero—profile linear mini-plate.
Figure 5A:
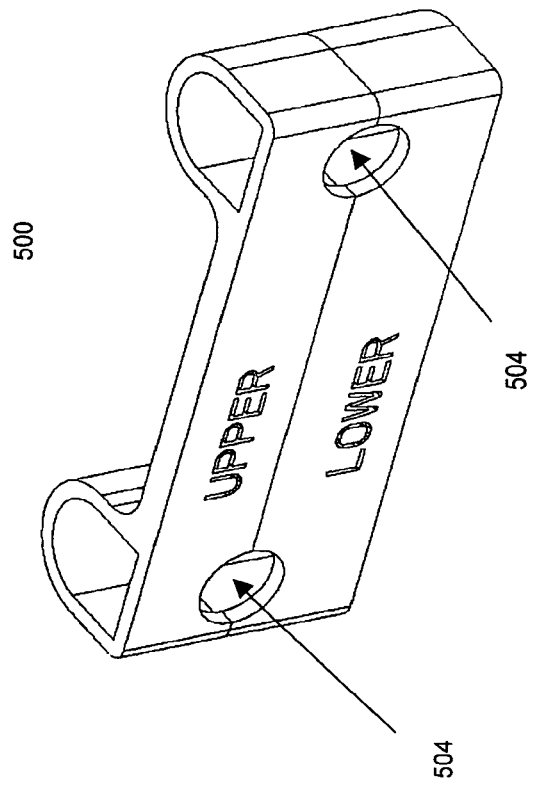

FIG. 5A illustrates the zero-profile horizontal linear mini-plate 500. Note the slots for placement of the BDFT screws 1000. On the anterior surface are slots 504 for the driving pinion screws. FIG. 5B illustrates that the plate 500 consists of upper and lower portions 500a, 500b which articulate with each other via interdigitation of alignment pins 502 and recesses 503. FIG. 5C illustrates the integration of the BDFT screws 1000 into the mini-plate 500. FIG. 5D illustrates the placement of the plate-BDFT construct into the intervertebral space. After the construct is placed into the intervertebral space, the screws 1000 are expanded bi-directionally in order to engage the vertebral bodies 400. This construct can be surgically placed via anterior or posterior approaches.

FIGS. 6A-G illustrate a zero-profile triangular mini-plate 600. In this embodiment the plate encompasses all three triangularly situated BDFT screws 1000. The posteriorly placed BDFT screw 1000 is expanded with a centrally placed drive screw/pinion with a long stem which extends posteriorly.

Figure 6B:
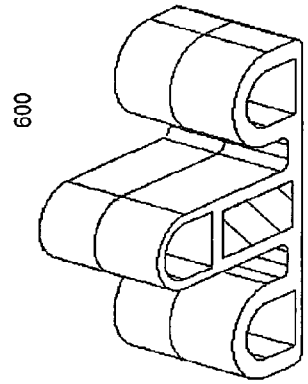
FIGS. 6A through 6G illustrate different views of the zero-profile triangular mini-plate, its integration with BDFT screws and incorporation into the vertebral bodies.
Figure 6A:
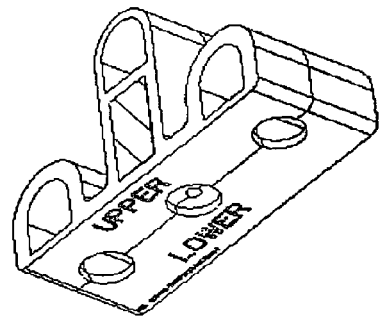
Figure 6C:
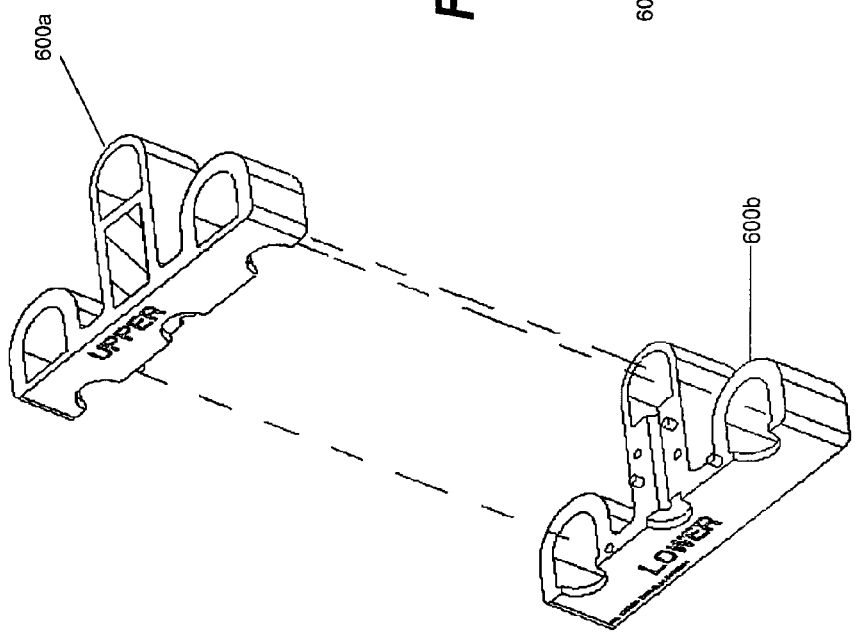
Figure 6F:
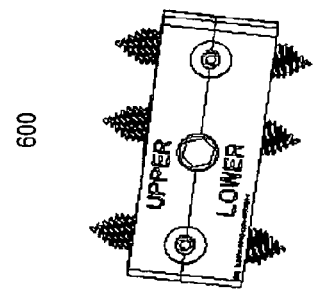
Figure 6D:
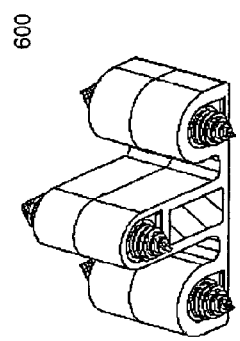
Figure 6E:
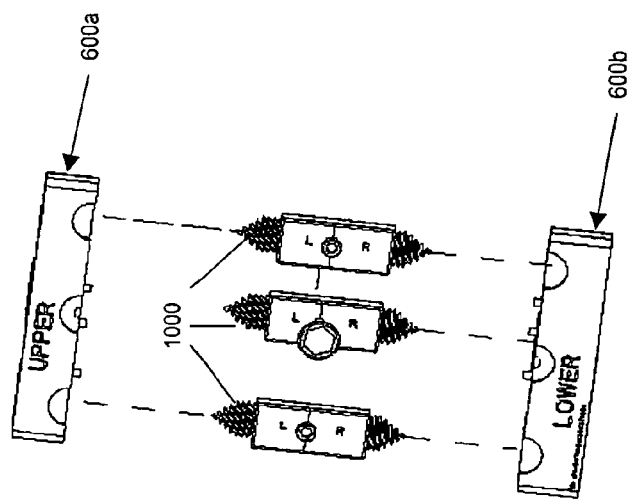
Figure 6G:
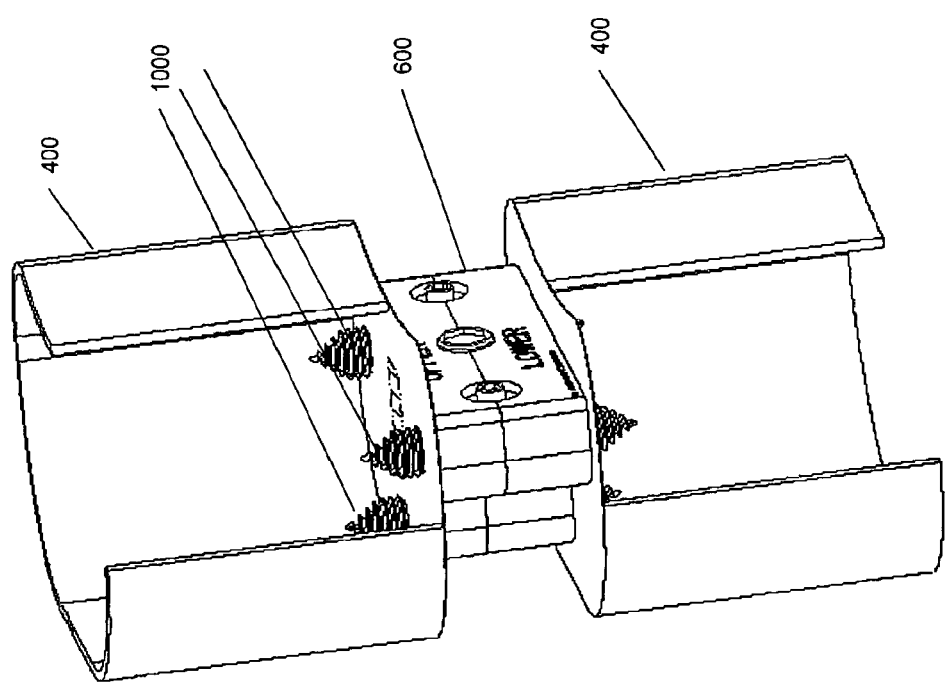
Figure 6I:
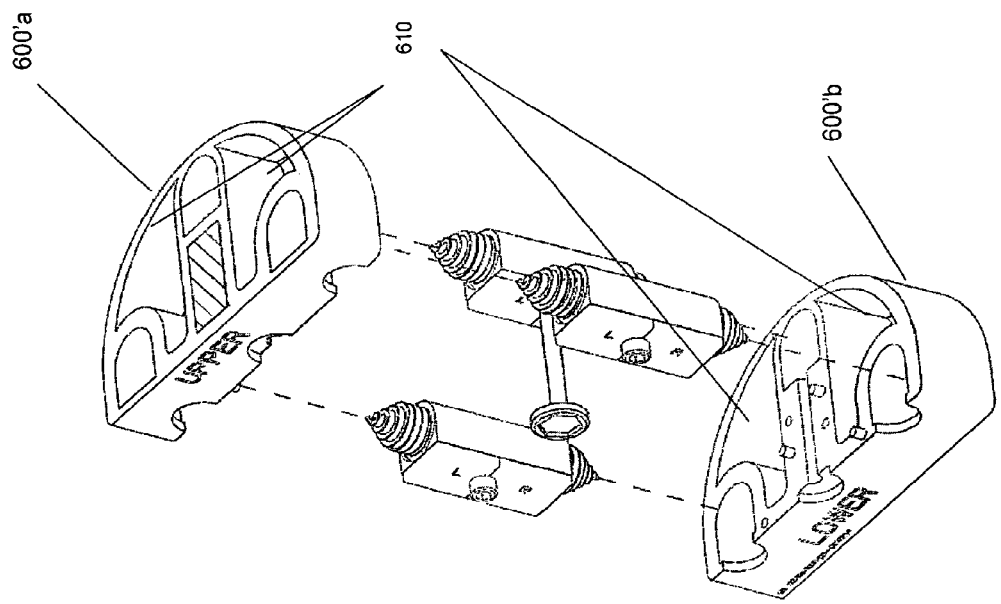
FIGS. 6H and 6I illustrate different views of the three-in-one device combining a zero-profile horizontal mini-plate, a cage with incorporated slots for the placement of bone material, and BDFT screws FIGS. 7 A and 7B illustrate the lumbar two-dimensionally expanding intervertebral fusion device (IBFD) with incorporated BDFT screws.
Figure 6H:
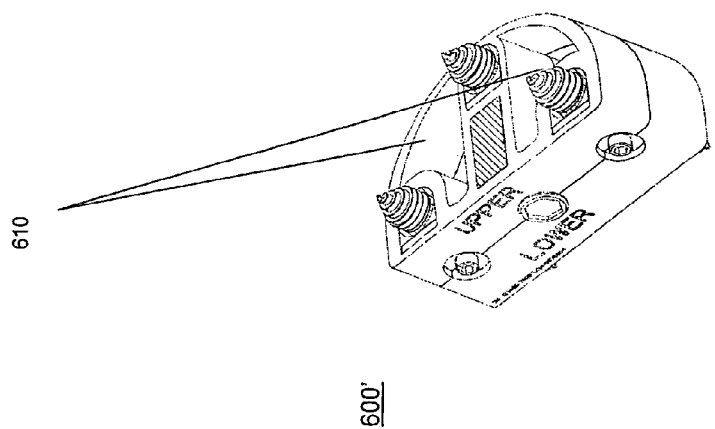

As illustrated in FIGS. 6H and 6I this embodiment 600' could be made hollow to accommodate the packing of bone material and can actually function as a combined three-in-one fusion cage/plate/BDFT screw construct. Note that this plate embodiment 600' also has upper and lower components similar to 600a, 600b (FIGS. 6A-C). Preferably, plates 600'a and 600'b, however, include slots 610 for placement of bone material. FIGS. 6D-F illustrate the incorporation of the BDFT screws 1000 into the triangular mini-plate 600. FIG. 6G illustrates the positioning of the triangular mini-plate 600 with incorporated expanded screws 1000 into adjacent vertebral bodies 400.

Figure 7A:
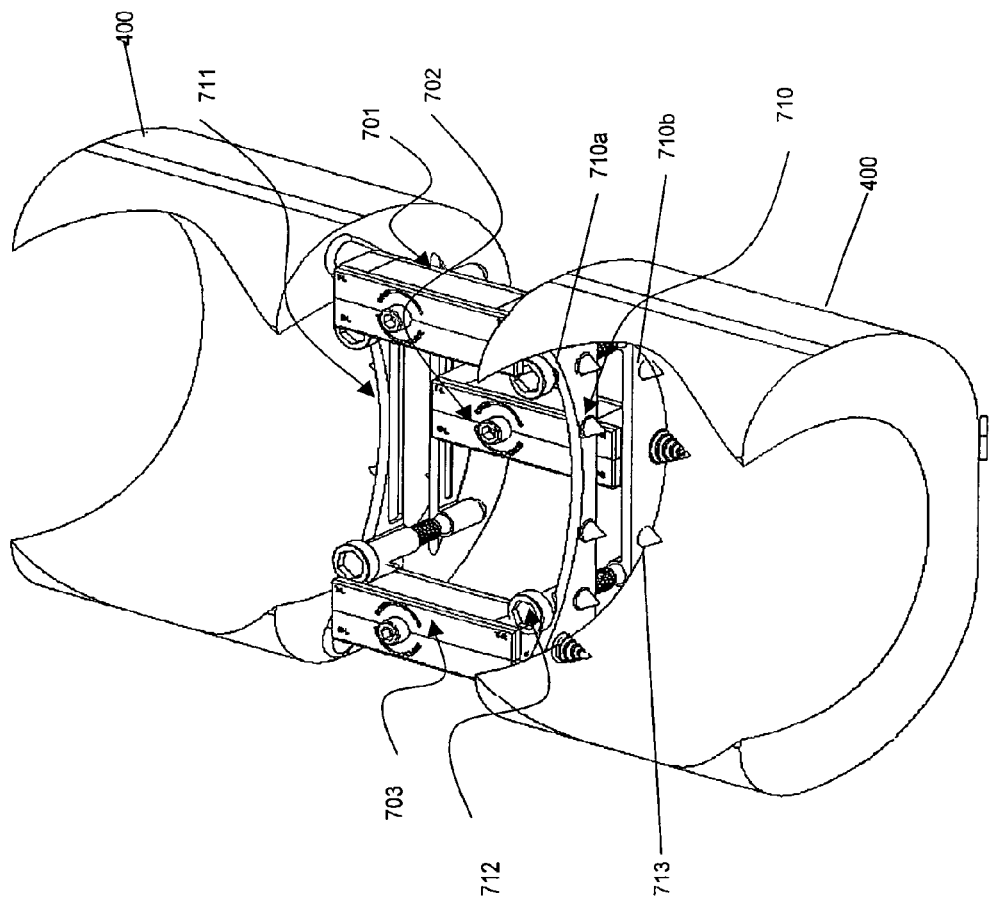
Figure 7B:
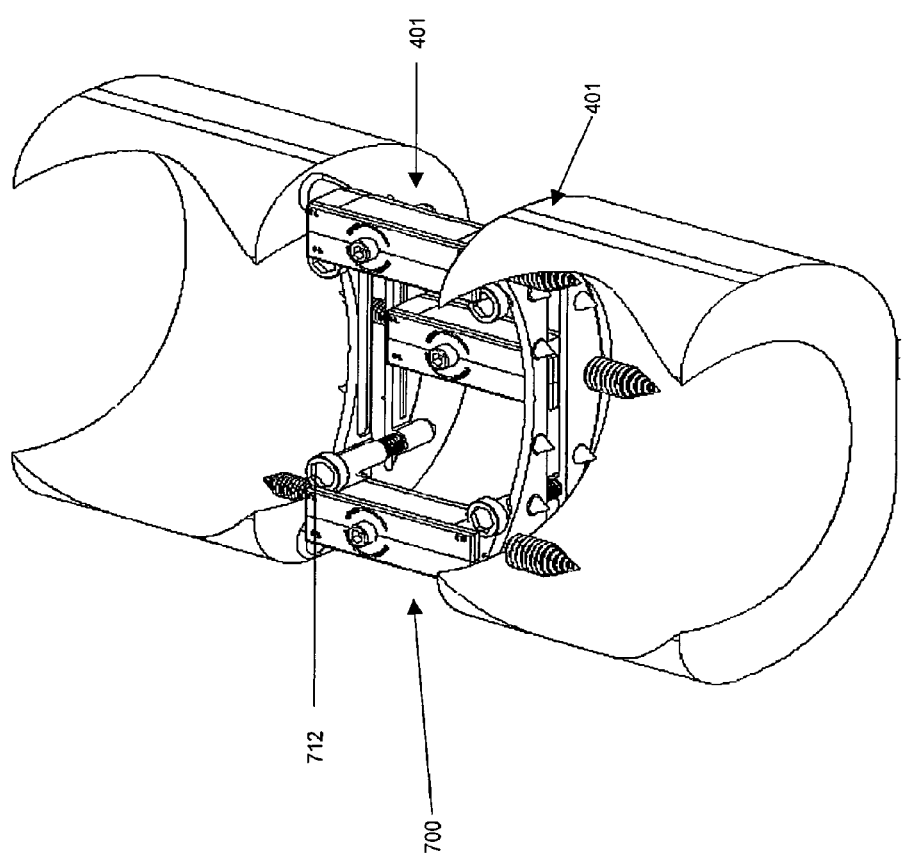

FIGS. 7A and 7B illustrate a boomerang shaped thoracolumbar IBFD 700 with ratchetable titanium or PEEK shells 710, 711 which can expand geometrically in two dimensions. FIG. 7A illustrates the BDFT screws 701, 702, 703 in partially expanded position. FIG. 7B illustrates the BDFT screws 701, 702, 703 in fully expanded position. The outer shells 710, 711 themselves when ratcheted width-wise have titanium or PEEK spikes 713 inserting themselves into and purchasing the endplates 401, thus securing permanent integration into the vertebral endplates 401. The outer shell 710, 711 surfaces can be treated with hydroxyappetite to facilitate bone incorporation. These shells are fully described in our previous PCT Patent Application PCT/US2005/016493, filed May 11, 2005.

The IBFD device 700 has four shells and a plurality of spikes 713. The height can be modified by adjusting four fixed height screws 712. Sequential turning of these screws 712 leads to height expansion between the rostral and caudal shells 710, 711 by widening the distance between their superior and inferior shells 710a, 710b. Once the IBFD 700 is properly positioned in the interspace the spikes 713 engage and purchase the vertebral endplates 401. The three incorporated BDFT screws 701, 702, 703 are turned clockwise leading to anterior and middle column engagement of the vertebral bodies 400 above and below the disc space. The BDFT screws 701, 702, 703 are strategically placed; one on each side of the superior shell 710a and one centrally on the inferior shell 710b. This captures anterior and middle columns of the vertebral column increasing spinal stability. After the BDFT screws 701, 702, 703 are successfully purchased within the vertebral bodies 400, bone fusion substances are placed/packed or poured, into the inner aspects of the device 700 and its surrounding intervertebral space.

An alternative thoracolumbar IBFD embodiment not illustrated expands in two dimensions and has the additional feature of an incorporated expansile porous elastometric sheath molded to the inner aspects of the titanium shells. Within the balloon is a port with or without an attached microsilastic catheter through which bone fusion material can be injected. Supplemental bone fusion material can be added to the surrounding area of the device to further enhance fusion. Furthermore for certain patients where applicable, a rapid fusion can be effected by the instillation of methyl-methacrylate A similar embodiment for a cervical IBFD is based on our previously described two-dimensional cervical expansion device in PCT Patent Application PCT/US2005/016493, filed May 11, 2005.

The engagement of the IBFD shell spikes 713 and the BDFT screws 701, 702, 703 into the vertebral bodies 400 above and below the device would obviate the need for any kind of anterior plating system.

Figure 8C:
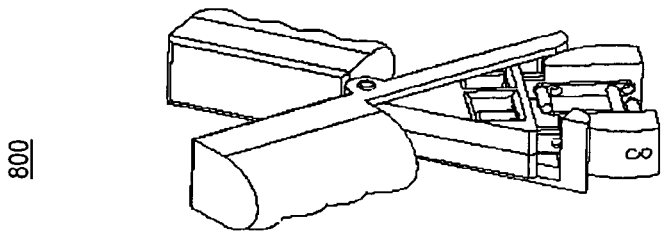
FIGS. 8A-N illustrate the facet joint calibrated stapling device which staples the inferior articulating facet with the superior articulating facet. Increasing degrees of torque calibration leads to increasing posterior column rigidity, whereas decreasing degrees of calibration leads to increasing flexibility.
FIGS. 8O and 8P illustrate four frontal and perspective views of the facet staple with sequential increasing calibrated positions leading to decreasing increments of joint motion/flexibility.
FIGS. 8Q and 8R illustrate the stapled inferior and superior interarticulating facets by the facet stapler.
Figure 8B:
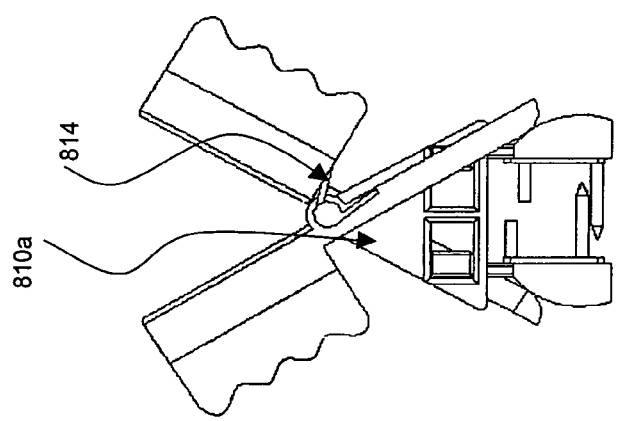
Figure 8A:
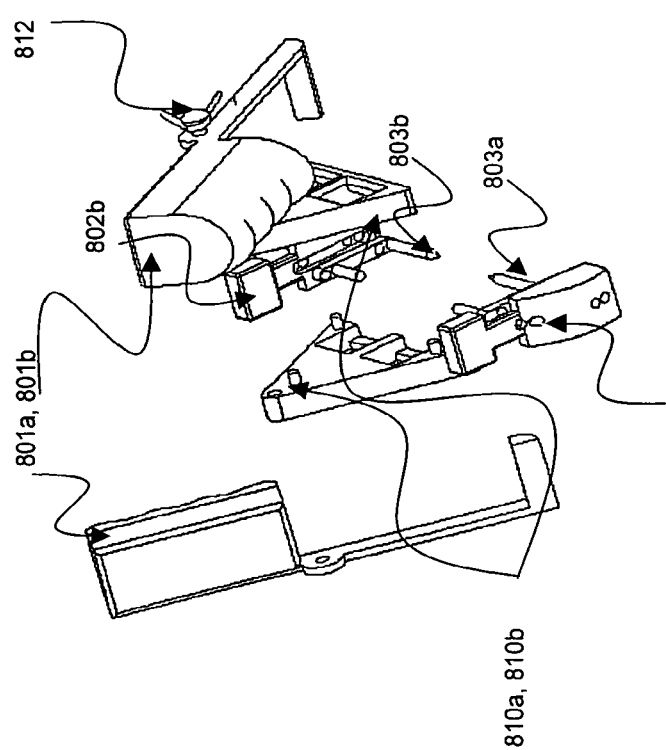

FIGS. 8A-N illustrate a calibrated facet joint stapler 800 which can be used to staple the thoracolumbar inferior and superior articulating facets with incremental torque degrees. Incrementally increasing the degrees of calibration modulates the extent of facet joint flexibility. This can be used as an option to provide posterior column support and can be used in an open, or percutaneous, endoscopic or fluoroscopic approach. Depending on the operative approach and the individual patient, facet stapling can be performed unilaterally or bilaterally.

Figure 8E:
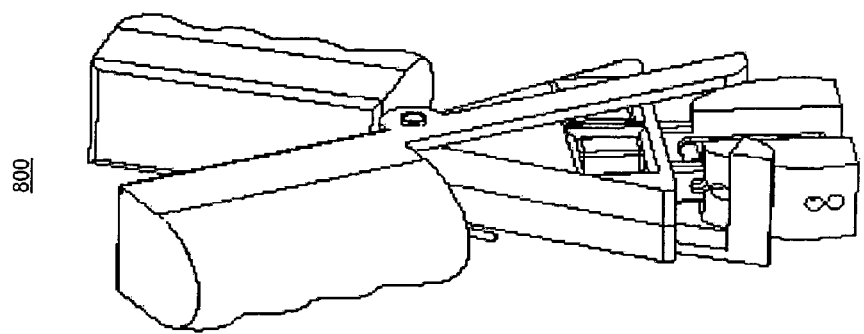
Figure 8D:
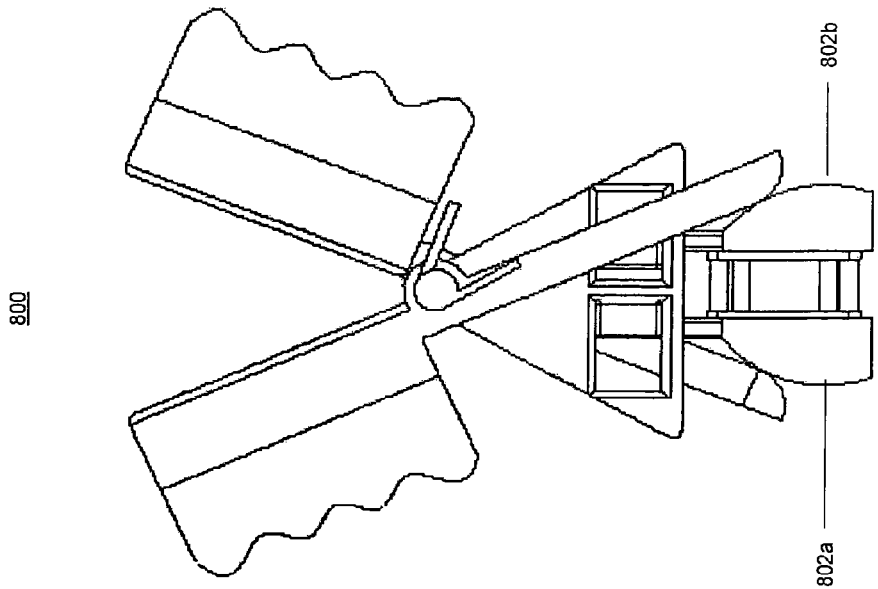

The stapling device 800 consists of two orthogonally placed levers 801a, 801b which open and close over a triangular fulcrum 810. The edges of the levers 801a, 801b are attached to left sand right staple cartridges 802a, 802b. Each cartridge 802a, 802b holds a titanium staple 803a, 803b in its slots. FIG. 8A illustrates an exploded view of the joint stapler 800 and its essential components. FIGS. 8B and 8C illustrate the stapler 800 in open position. FIGS. 8D and 8E illustrate the stapling device 800 and staples 803a, 803b in closed position. FIGS. 8F and 8G illustrate the stapling device 800 and 803a, 803b staples in closed, staple released, position. FIG. 8H-J illustrate the components of the lever 801a, 801b which includes the grip handle 815, arm 816, rounded wedge 817 and fulcrum screw hole 818. FIGS. 8K and 8L illustrate the details of the cartridge 802a, 802b including its slot for the fulcrum 810 and staples 803a, 803b. FIGS. 8M and 8N illustrate the details of the fulcrum 810 which include right and left cartridge slots 820a, 820b and fulcrum screw 812 and mating alignments. Most importantly it has four incremental calibration slots for incremental degrees of facet joint stapling. Also illustrated are spring anchors 814.

Figure 8P:
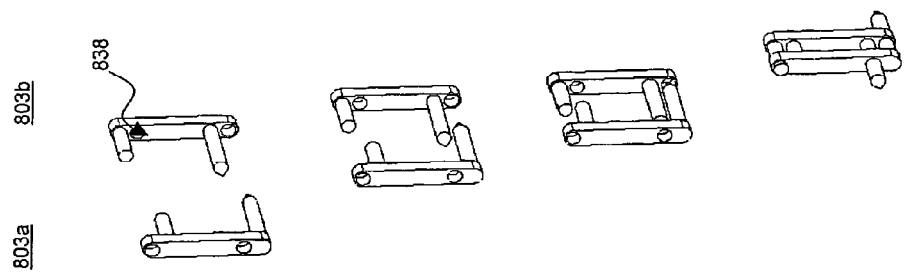
Figure 8O:
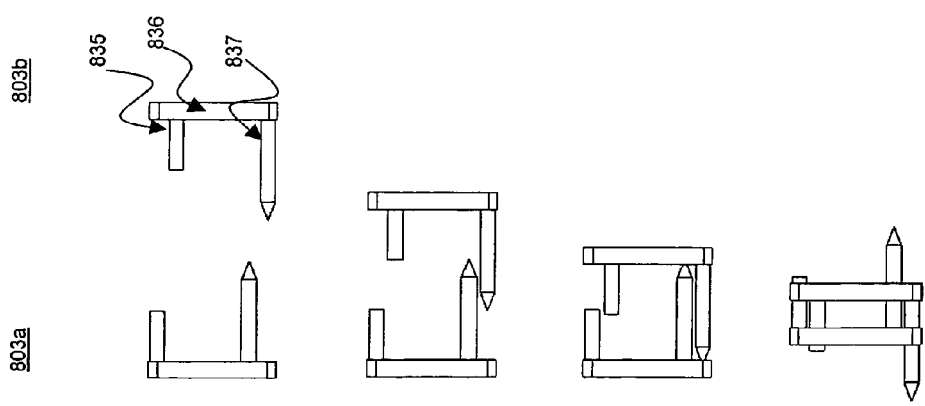

FIGS. 8O and 8P illustrate frontal and perspective views, respectively of the two opposing titanium facet staples 803a, 803b. Each staple 803a, 803b consists of a bracket 836, a nail 837 and an alignment pin 835. Illustrated are four sequential calibrated tightening positions of the opposing staples 803a, 803b. Increasing the calibrated opposition of the two staples 803a, 803b leads to increasing opposition of the facet joints and hence increasing rigidity, and decreasing flexibility. Each staple 803a, 803b has two alignment recesses 838. The opposition of these staples 803a, 803b around the facet joint forms a rectangular facet joint enclosure.

Figure 8R:
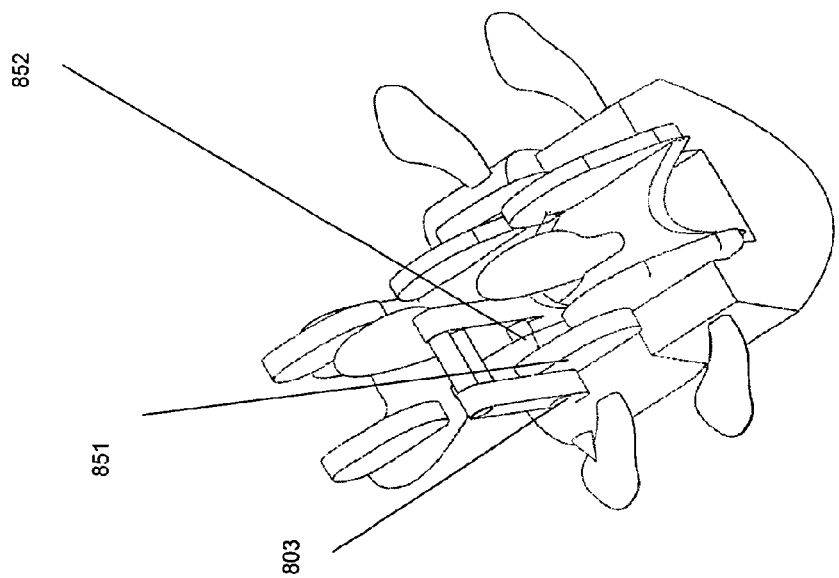
Figure 8Q:
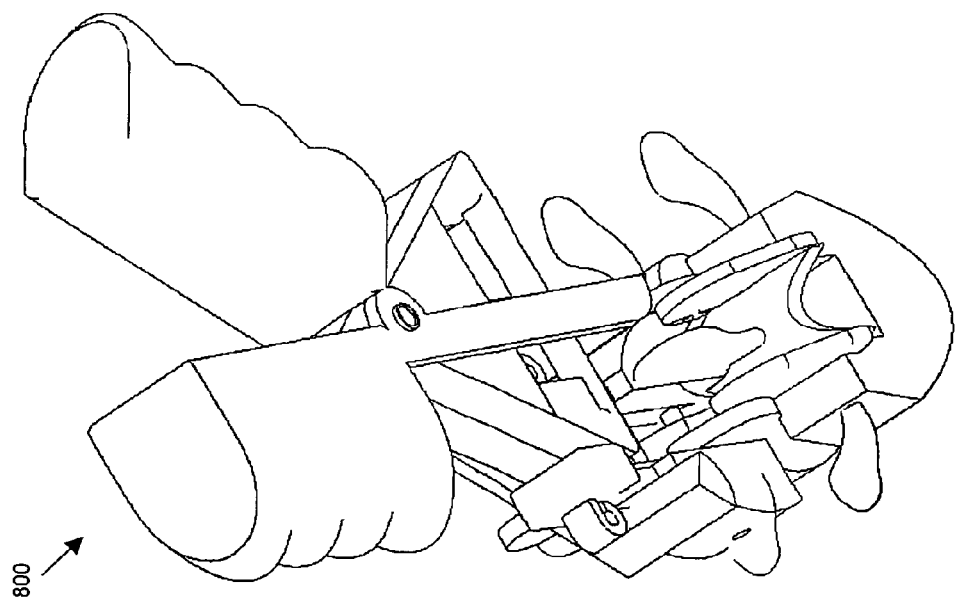

FIGS. 8Q ad 8R illustrate the stapled inferior and superior articulating facets 851, 852. FIG. 8R illustrates the application of the facet stapler 800 on the facets 851, 852 introducing the facet staple 803. The facet staple is used to join the exterior articulating facet 851 and the interior articulating facet 852.

2. The Surgical Method

The surgical steps necessary to practice the present invention will now be described.

The posterior lumbar spine implantation of the BDFT screws 1000, plate and IBFD can be implanted via a previously described posterior lumbar interbody fusion procedure (PLIF) or posterior transforaminal lumbar interbody fusion procedure (TLIF). The procedure can be performed open, microscopic, closed, tubular or endoscopic. Fluoroscopic guidance can be used with any of these procedures.

After the adequate induction of anesthesia, the patient is placed in the prone position.

A midline incision is made for a PLIF, and one or two parallel paramedian incisions or a midline incision is made for a TLIF. For the PLIF a unilateral or bilateral facet sparing hemi-laminotomy is created to introduce the BDFT screws 1000, plates or IBFD into the disc space after it is adequately prepared. For the TLIF procedure, after a unilateral dissection and drilling of the inferior articulating surface and the medial superior articulating facet, the far lateral disc space is entered and a circumferential discectomy is performed. The disc space is prepared and the endplates exposed.

There are then multiple embodiments to choose from for an intervertebral body fusion. With the first and simplest choice, under direct or endoscopic guidance one BDFT screw 1000 or three BDFT screws 1000 can be placed in a triangulating manner encompassing the anterior and middle vertebral columns (FIGS. 4A-C). The screws 1000 are then maximally expanded purchasing and uniting the vertebral bodies above and below the disc space. Bone material or an alternative intervertebral fusion device can then be packed into the disc space. The casing of the screws 1000 prevents subsidence of the vertebral bodies. An additional option in the posterior lumbar spine is to place a mini-plate dorsally underneath the thecal sac to prevent bone migration into the nerves. In addition via a TLIF approach a triangular mini-plate/cage construct can be inserted, and then the BDFT screws 1000 maximally expanded. This is a very simple and practical supplemental or stand-alone intervertebral fusion device.

Using an alternative IBFD option, utilizing specialized forceps the two-dimensional expanding thoracolumbar expandable IBFD 700 (FIGS. 7A and 7B) is introduced into the disc space. The final dimension expansion in all embodiments leads to purchasing of the spikes into the vertebral endplates. The BDFT screws 1000 are then driven directly into rostral and caudal vertebral bodies across the intervertebral space. Then bone fusion material; autologous, allograft, bone matrix protein, BMP, rh-BMP, paste or other similar currently available or specially designed osteoconductive substances can be placed into the device and the surrounding intervertebral space. In embodiments with an incorporated viscoelastic balloon sheath, prior to engaging the screws the expandable elastometric sheath/balloon is filled with bone fusion material as mentioned above. If desirable, further material, can be placed outside its confines within the intervertebral space.

If further posterior column stability or rigidity is required, unilateral or bilateral, single level or multiple level facet screw stapling can be performed under open, microscopic flouroscopic or endoscopic vision. Radiographic confirmation of staple position is obtained. Calibrated stapling leads to opposition of the facet joints with incremental degrees of joint opposition. This can lead to variable degrees of posterior column rigidity and/or flexibility.

The anterior lumbar spine implantation of solitary BDFT screw(s) 1000, BDFT screws incorporated into a horizontal linear or triangular mini-plate, or the IBFD/BDFT screw embodiment for L4/5 and L5/S1 interspaces can be performed on the supine anesthetized patient via previously described open micropscopic or endoscopic techniques. Once the disc space is exposed and discectomy and space preparation is performed, placement of one, two or three BDFT screws 1000 with or without a ventral mini-plate, or placement of two dimensionally expanding IBFD with or without expansile elastometric sheaths and their incorporation is identical to that performed for the posterior approach.

The posterior placement of the BDFT screws 1000 alone or combined with mini-plates or with IBFD embodiments into the thoracic spine can be performed via previously described transpedicular approaches; open or endoscopic. The anterior placement of the IBFD 700 into the thoracic spine can be accomplished via a trans-thoracic approach. Once disc space exposure is obtained via either approach, all of the above mentioned embodiments can be inserted. Engagement of the devices is identical to what was mentioned above.

For anterior placement of the cervical embodiments of the BDFT screw(s) 1000 with or without the horizontal linear or triangular cervical mini-plate, and the IBFD embodiments the anterior spine is exposed in the anesthetized patient as previously described for anterior cervical discectomies. Once the disc space is identified, discectomy is performed and the disc space prepared. Implantation and engagement of all devices is identical to that described for the anterior lumbar and thoracic spines.

The present invention may provide an effective and safe technique that overcomes the problems associated with current tanspedicular-based thoracic and lumbar fusion technology, and with current vertical cervical plating technology, and for many degenerative stable and unstable spine diseases, and could replace many pedicle screw-based and anterior vertical-plate based instrumentation in many but not all degenerative spinal conditions. Calibrated facet joint screw staples can facilitate flexible fusions and could replace current static trans-facet screws.

To our knowledge there has not been any other previously described bi-directional screw for use in the spine, other joints, or for any commercial or carpentry application. The bi-directional screw 1000 described herein may indeed have applications in general commercial, industrial and carpentry industries. To our knowledge the description of zero to subzero profile anterior or posterior horizontal spinal plates which traverse the diameter of the disc space has not been previously described. To our knowledge an intervertebral three-in-one construct combining bone cage, plate and screws has not been previously reported. To our knowledge calibrated facet joint staples 803a, 803b have not been previously described.

We claim:
1. A self-drilling screw apparatus, which comprises:
an intervertebral cage comprising a shell;
a first screw member having a tapered end and a threaded body disposed within the shell;
a second screw member having a tapered end and a threaded body disposed within the shell; and
a drive mechanism for driving the first and second screw members from the shell, the drive mechanism including a drive screw disposed at least partially within the intervertebral cage, and a pinion that is responsive to the rotation of the drive screw and that simultaneously drives the first and second screw members from the intervertebral cage and simultaneously rotates the first and second screw members as the first and second screw members are driven from the intervertebral cage.

2. An apparatus according to claim 1 wherein the shell includes a first aperture threaded in a first direction for the first screw member and a second aperture threaded in the opposition direction for the second screw member.

3. An apparatus according to claim 1 wherein the drive mechanism includes;

a gear rotated by the pinion, and the rotation of the gear imparts rotation to the first screw member and the second screw member.

4. An apparatus according to claim 3 wherein the drive screw includes an accessible head that is rotated in order to drive the first and second screw members from the shell.

5. An apparatus according to claim 3 where in the gear includes keyways for the first screw member and the second screw member.

6. An apparatus according to claim 3 which further includes end caps and a top for enclosing the shell.

7. An apparatus according to claim 1 wherein the first screw member is of a diameter smaller than the diameter of the second screw member; and wherein the second screw member includes a hollow threaded portion that receives a portion of the threaded body of the first screw member.

8. An apparatus according to claim 7 wherein the threaded body of the first screw member is threaded in a first direction and the threaded body of the second screw member is threaded in the opposite direction.

9. An apparatus according to claim 8 wherein the drive screw includes an accessible head that is rotated in order to drive the first and second screw members from the shell.

10. An apparatus according to claim 1 which further includes end caps and a top for enclosing the shell.

11. An apparatus according to claim 1 wherein the apparatus is used to join together two members,
wherein the members are selected from the group which includes bones, portions of the spinal column, vertebral bodies, wood, building materials, metal, masonry or plastics.

12. An apparatus according to claim 1 wherein the first screw member and the second screw member extend bi-directionally from opposite ends of the shell.

13. An apparatus according to claim 1 and further comprising:
a first plate with a predetermined pattern of apertures for the screw apparatuses; and
a second plate with a predetermined pattern of apertures for the screw apparatuses.

14. An apparatus according to claim 13 wherein the apparatus is used to join together a pair of vertebral bodies.

15. An apparatus according to claim 13 wherein the plates include at least one pin and one slot for aligning the plates.

16. An apparatus according to claim 14 wherein the first plate and the second plate include slots for the placement of bone material.

17. The apparatus according to claim 1 wherein the first screw member is of a diameter smaller than the diameter of the second screw member; and wherein the second screw member includes a hollow threaded portion that receives a portion of the threaded body of the first screw member.

18. The apparatus according to claim 1 wherein the shell includes a first aperture threaded in a first direction for the first screw member and a second aperture threaded in the opposition direction for the second screw member.

19. The apparatus according to claim 1, wherein the first screw member and the second screw member extend bi-directionally from opposite ends of the shell, and
wherein the drive mechanism is configured such that actuation of the drive mechanism simultaneously drives the first screw member and the second screw member an equal distance from the opposite ends of the shell.

20. The self-drilling screw apparatus of claim 1, wherein the intervertebral cage includes a top wall, a bottom wall, and two sidewalls defining at least one open space capable of receiving the shell.

21. The self-drilling screw apparatus of claim 1, wherein the shell is disposed within the intervertebral cage and the drive mechanism is configured to drive the first and second screw members from the shell and the intervertebral cage.

22. An apparatus comprising an artificial expansile disc having first and second shells and an expansion mechanism positioned between the first and second shells and configured to expand the artificial expansile disc, wherein the expansion mechanism comprises a turning mechanism configured to drive expansion between the first shell and the second shell in response to turning the turning mechanism, wherein the artificial expansile disc is configured to be introduced into an intervertebral space with the first and second shells engaging opposing vertebral bodies when inserted into the intervertebral space and the expansion mechanism has a tool engagement portion positioned and configured to be engaged by a tool extending along a direction of insertion for rotating the turning mechanism, wherein each of the first and second shells comprises a first set of engagement features extending from the first and second shells that are configured for engaging vertebral endplates of the opposing vertebral bodies to hold the artificial expansile disc in place and a second set of engagement features extending from the first and second shells that are configured for engaging the vertebral endplates of the opposing vertebral bodies to hold the artificial expansile disc in place, wherein the second set of engagement features are larger than the first set of engagement features, extend further than the first set of engagement features, and have substantially conical tips configured for piercing the vertebral endplates when introduced into the intervertebral space and expanded.

23. An apparatus according to claim 22 wherein the artificial expansile disc can be adjusted in at least two directions in order to facilitate bone fusion of two adjacent segments.

24. The apparatus of claim 22, wherein the second set of engagement features comprise at least first and second screw members configured to be extended from the first shell into one of the vertebral endplates and at least third and fourth screw members configured to be extended from the second shell into another of the vertebral endplates.

25. The apparatus of claim 22, wherein the second set of engagement features extend from the first and second shells in directions substantially perpendicular to the first and second shells.

26. The apparatus of claim 22, wherein the first shell, the second shell, and the first set of engagement features extending from both the first and second shells comprise PEEK (poly-ether-ketone).

27. The apparatus of claim 22, wherein the artificial expansile disc can expand geometrically in two dimensions.

28. The apparatus of claim 22, wherein each of the first and second shells define holes into which the second set of engagement features at least partially extend.

29. The apparatus of claim 22, wherein each of the first and second shells define holes into which the second set of engagement features at least partially extend and the second set of engagement features extend from the holes of the first and second shells in directions substantially perpendicular to the first and second shells and wherein the first set of engagement features are more numerous than the second set of engagement features.

30. The apparatus of claim 22, wherein the first shell, the second shell, and the first set of engagement features extending from both the first and second shells comprise PEEK (poly-ether-ketone), wherein each of the first and second shells define screw holes, and wherein the second set of engagement features comprise screw members extendable through the holes at least partially into the vertebral endplates.

31. The apparatus of claim 22, and further comprising means for expanding geometrically in a second direction.

32. A self-drilling screw apparatus comprising:
an intervertebral cage including a top wall, a bottom wall, and two sidewalls defining at least one open space capable of receiving bone filling for biological bone fusion;
a first screw member having a tapered end and a threaded body disposed within the intervertebral cage;
a second screw member having a tapered end and a threaded body disposed within the intervertebral cage, wherein the first screw member has a diameter that is smaller than a diameter of the second screw member, and wherein the second screw member includes a hollow threaded portion that receives a portion of the threaded body of the first screw member; and
a drive mechanism configured to simultaneously drive the first and second screw members from the intervertebral cage,
wherein the drive mechanism includes:
a drive screw disposed at least partially within the intervertebral cage;
a pinion that is responsive to the rotation of the drive screw and that simultaneously drives the first and second screw members from the intervertebral cage and simultaneously rotates the first and second screw members as the first and second screw members are driven from the intervertebral cage.

* * * * *